US011390862B2

(12) United States Patent
Chen et al.

(10) Patent No.: US 11,390,862 B2
(45) **Date of Patent: *Jul. 19, 2022**

(54) PROTEINASES WITH IMPROVED PROPERTIES

(71) Applicant: New England Biolabs, Inc., Ipswich, MA (US)

(72) Inventors: Minyong Chen, Ipswich, MA (US); James C. Samuelson, Newburyport, MA (US); Ming-Qun Xu, Hamilton, MA (US); Aihua Zhang, Ipswich, MA (US); Margaret Heider, Ipswich, MA (US); Pingfang Liu, Ipswich, MA (US)

(73) Assignee: New England Biolabs, Inc., Ipswich, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/129,112

(22) Filed: Dec. 21, 2020

(65) Prior Publication Data

US 2021/0115427 A1 Apr. 22, 2021

Related U.S. Application Data

(63) Continuation of application No. 16/718,880, filed on Dec. 18, 2019, now abandoned.

(60) Provisional application No. 62/782,436, filed on Dec. 20, 2018, provisional application No. 62/782,716, filed on Dec. 20, 2018.

(51) Int. Cl.

| | |
|---|---|
| ***C12N 9/64*** | (2006.01) |
| ***C12N 9/12*** | (2006.01) |
| ***C12P 19/34*** | (2006.01) |

(52) U.S. Cl.

CPC ......... *C12N 9/6424* (2013.01); *C12N 9/1241* (2013.01); *C12P 19/34* (2013.01); *C12Y 207/07019* (2013.01); *C12Y 304/21064* (2013.01)

(58) Field of Classification Search

CPC .................................................... C12N 9/6424

USPC ......................................................... 435/212

See application file for complete search history.

(56) References Cited

U.S. PATENT DOCUMENTS

| | | | |
|---|---|---|---|
| 4,980,288 | A | 12/1990 | Bryan et al. |
| 5,246,849 | A | 9/1993 | Bryan et al. |
| 5,340,735 | A | 8/1994 | Christianson et al. |

FOREIGN PATENT DOCUMENTS

| | | | |
|---|---|---|---|
| WO | 9628556 | A2 | 9/1996 |
| WO | 2005087922 | A1 | 9/2005 |

OTHER PUBLICATIONS

Crowe et al, Improved cloning efficiency of polymerase chain reaction (PCR) products after proteinase K •digestion. 184 Nucleic Acids Research, vol. 19, No. 1.*

ThermoFisher Scientific Proteinase K, recombinant, PCR grade. Downloaded Dec. 20, 2021.*

Tenhunen, Mol. Cell Probes., Dec. 1989: 3(4): 391-396.

Umapathi, et al., (2018). Scaling Electrowetting with Printed Circuit Boards for Large Area Droplet Manipulation. MRS Advances, 3(26), 1475-1483. doi: 10.1557/adv.2018.331.

Zhang et al., Scientific Reports, 8:15887, 2018.

Moran, FEMS Microbiology Letters 197, 2001, 59-63.

Liao, et al., BMC Biotechnology, 2007, 7:16.

Geneseq Database accession No. BBT95540 Mar. 15, 2015.

Betzel, et al, Eur J Biochem. 1988 178:155-71.

Betzel, et al., Acta Crystallogr B. 1988 44:163-72.

Pähler et al, EMBO J. 1984 3:1311-14.

Hu, et al., Evolutionary Biology 2004: 1204-1214.

* cited by examiner

*Primary Examiner* — Sheridan Swope

(74) *Attorney, Agent, or Firm* — New England Biolabs, Inc; Harriet M. Strimpel

(57) ABSTRACT

Provided herein is a thermolabile proteinase and methods of using the same. In some embodiments, the thermolabile proteinase may comprise an amino acid sequence that is at least 90% identical to any of SEQ ID NOs:1-11 and at least one amino acid substitution in helix 3. The thermolabile proteinase is active at a temperature in the range of 4° C.-40° C. and is inactivated by raising the temperature to above 50° C., where the proteinase is substantially inactive at 65° C.

8 Claims, 16 Drawing Sheets

Specification includes a Sequence Listing.

FIG. 3A
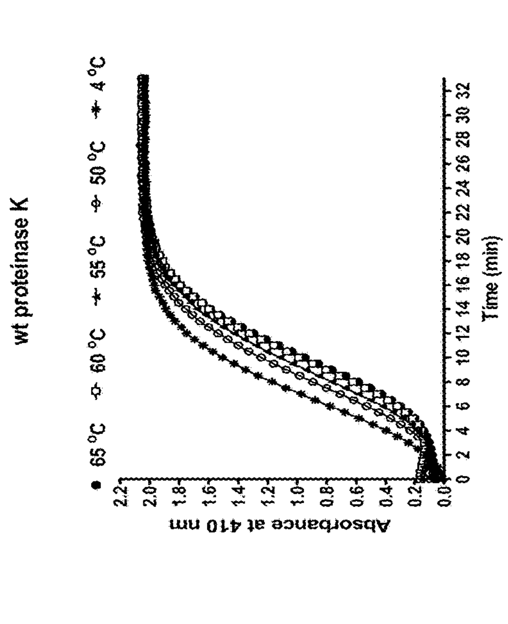
FIG. 3B
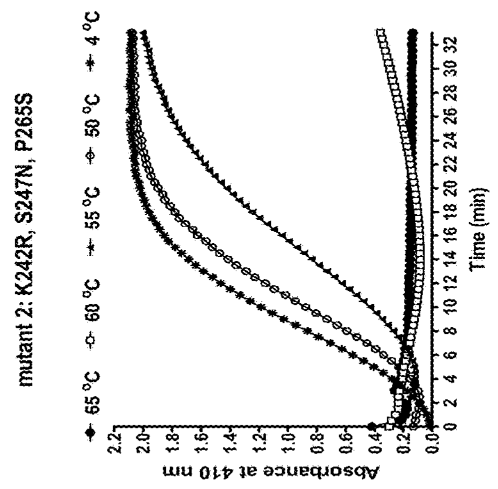
FIG. 3C
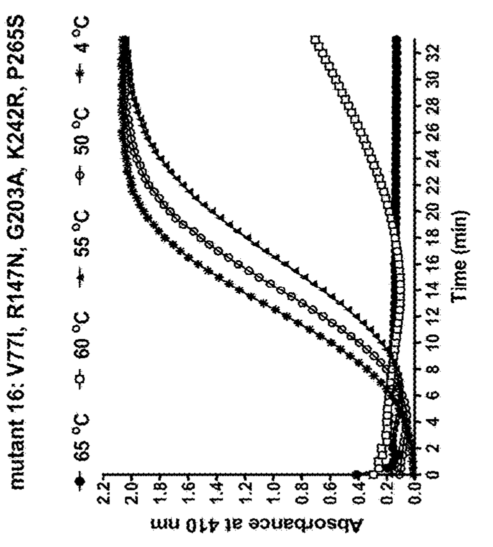
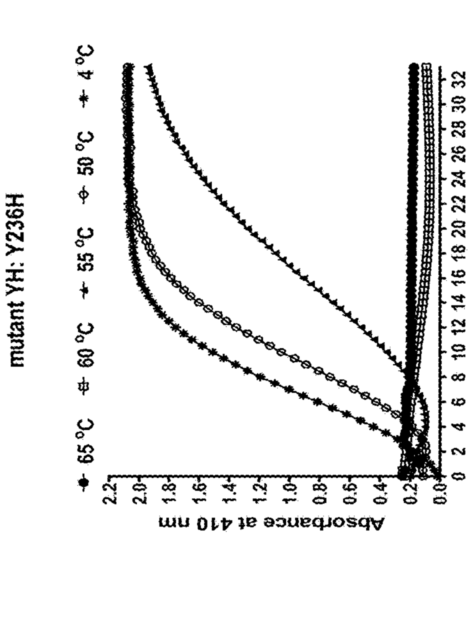
FIG. 3D
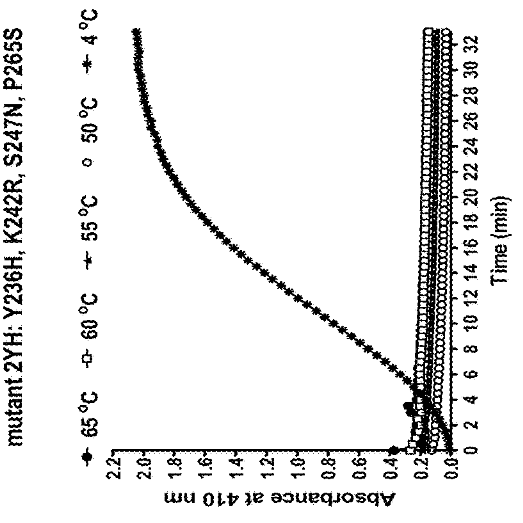
FIG. 3E
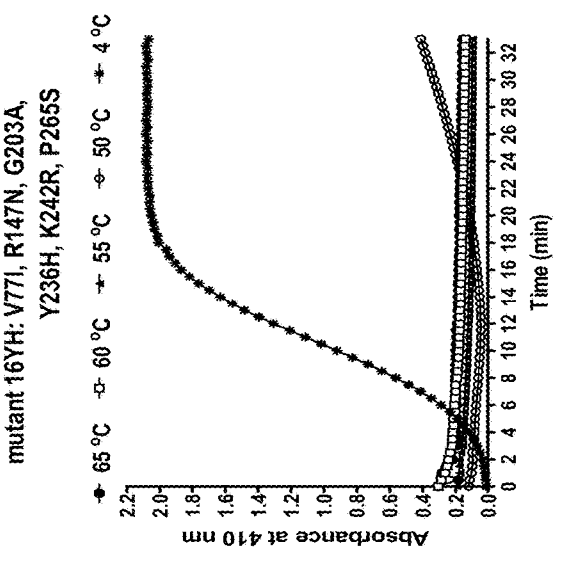
FIG. 3F

Y236
↓

---VAGLAAYL---- wt (SEQ ID NO: 12)
---VAGLAAHL---- Y236H (SEQ ID NO: 13)
---VAGLAAQL---- Y236Q (SEQ ID NO: 14)
---VAGLAAKL---- Y236K (SEQ ID NO: 15)
---VAGLAAEL---- Y236E (SEQ ID NO: 16)
---VAGLAARL---- Y236R (SEQ ID NO: 17)
---VAGLAAGL---- Y236G (SEQ ID NO: 18)
---VAGLAAFL---- Y236F (SEQ ID NO: 19)
---VAGLAAVL---- Y236V (SEQ ID NO: 20)
---VAGLAADL---- Y236D (SEQ ID NO: 21)
---VAGLAATL---- Y236T (SEQ ID NO: 22)
---VAGLAALL---- Y236L (SEQ ID NO: 23)
---VAGLAAIL---- Y236I (SEQ ID NO: 24)
---VAGLAAML---- Y236M (SEQ ID NO: 25)
---VAGLAASL---- Y236S (SEQ ID NO: 26)
---VAGLAAWL---- Y236W (SEQ ID NO: 27)
---VAGLAAPL---- Y236P (SEQ ID NO: 28)
---VAGLAAAL---- Y236A (SEQ ID NO: 29)
---VAGLAANL---- Y236N (SEQ ID NO: 30)
---VAGLAACL---- Y236C (SEQ ID NO: 31)

FIG. 8A

PROTEINASES WITH IMPROVED PROPERTIES

CROSS-REFERENCE

This application is a continuation of U.S. application Ser. No. 16/718,880, filed Dec. 18, 2019, which claims priority to U.S. Provisional Application No. 62/782,436, filed Dec. 20, 2018, and U.S. Provisional Application No. 62/782,716, filed Dec. 20, 2018, the contents of which are hereby incorporated in their entirety by reference.

BACKGROUND

Endopeptidases are proteolytic peptidases that cleave peptide bonds between internal amino acids in proteins. These enzymes are classified as proteases. Proteases, including peptidases, are found ubiquitously in prokaryotes and eukaryotes. For example, at least 16 superfamilies of serine proteases have been described, each containing many families of proteins with evidence of convergent evolution in their protein structure. Serine proteases have been used in an industrial context, for example, in detergents. In this context, serine protease have been mutated to increase their thermostability (see for example, U.S. Pat. Nos. 4,980,288, 5,246,849 and 5,340,735). Serine proteases have also been used for molecular biology applications, for example, in the preparation of nucleic acid samples from cell isolates. To this end, a highly thermostable Proteinase K (also referred to as an endopeptidase K belonging to the peptidase family S8) from *Engyodontium album* (*Tritirachium album*) is commercially available and has a broad specificity for breaking down proteins with activity over a wide temperature range. In many applications, Proteinase K should be completely removed from a sample following its use and prior to subsequent reactions, for example, reactions using nucleic acid enzymes. Indeed, the use of Proteinase K in multi-step enzymatic workflows is adversely affected by its relative thermostability, where the temperatures required to fully inactivate Proteinase K often adversely affect the substrate (nucleic acid) structure. For example, temperatures above 65° C. result in partial denaturation of double stranded DNA that can result in DNA damage. Moreover, temperatures above 60° C. can result in hydrolysis of RNA (see e.g. Tenhunen, Mol. Cell Probes., 1989, 3 (4): 391-396).

While this problem can be solved in-part by purifying DNA or RNA away from the Proteinase K after treatment using beads or columns, many workflows, e.g., those that involve low abundance DNA or RNA samples, cannot afford the sample loss that occurs when separation methods are used.

SUMMARY

A protein is provided that in some embodiments is a proteinase that in some embodiments is a thermolabile proteinase. In general, the protein comprises: (a) an amino acid sequence that is at least 90% (e.g., at least 93% or at least 95%) but less than 100% identical to any of SEQ ID NOs:1-11; and (b) has at least one amino acid substitution at a position corresponding to amino acids 230-237 of SEQ ID NO:1, wherein the substitution is not isoleucine (I) at a position corresponding to position 230 of SEQ ID NO:1, wherein the substitution is not glycine (G) at a position corresponding to position 231, 234 or 235 of SEQ ID NO:1 and wherein the substitution is not phenylalanine (F) at a position corresponding to position 237 of SEQ ID NO:1.

For example, the protein may have an amino acid sequence that is a least 90% identical to the amino acid sequence of SEQ ID NO:1, wherein the protein has at least one amino acid substitution in SEQ ID NO:12. For example, the protein may have the amino acid sequence of SEQ ID NO:1 but with at least one amino acid substitution in helix 3 corresponding to position 225-240 in SEQ ID NO:1.

In some embodiments of the above described protein has at least one amino acid substitution at a position corresponding to any of 230, 233 or 236 of SEQ ID NO:1. More specifically, where the at least one amino acid substitution includes position 236 of SEQ ID NO:1, the tyrosine at that position may be substituted with an amino acid selected from the group consisting of serine, threonine, cysteine, methionine, proline, asparagine, glutamine, aspartate, glutamate, lysine, arginine, histidine, glycine, valine, alanine, leucine, isoleucine, tryptophan and phenylalanine. In another embodiment, the least one amino acid substitution corresponding to position 236 of SEQ ID NO:1 and is selected from the group consisting of an aspartate, glutamate, lysine, arginine and histidine. The protein may further comprise a substitution at one or more positions corresponding to 77, 147, 203, 242, 247 and 265 of SEQ ID NO:1 more specifically V77, R147, G203, K242, S247 and P265 (for example, at any 2, 3, 4, 5 or all 6 of these positions).

Properties of the protein may include having protease activity at temperatures of at least up to 40° C. with substantially reduced or no detectable protease activity after heat treatment at 65° C. (determined by, for example, gel electrophoresis) within a period of, for example, 40 minutes, 20 minutes, 15 minutes, 10 minutes or 5 minutes. For example, the protease activity of the proteinase at 65° C. may be less than 30%, 20%, 15%, 10%, 8%, 6% or 5% of the protease activity of the same proteinase at 4° C., and in one embodiment, the protease activity after heat treatment at 65° C. has preferably less than 10% of the protease activity at 4° C. after a 20 minute incubation.

In one embodiment, the protein may be characterized by thermolabile Proteinase K activity but is enzymatically inactive after heat treatment at a temperature of greater than 50° C. (for example at least 55° C., at least 60° C. or at least 65° C.). After heat treatment, the inactivated protease may be combined with an active enzyme that is not Proteinase K. The protein may be combined with one or more enzymes proteolyzed by the Proteinase K activity of the protein prior to heat inactivation. In some embodiments, the one or more proteolyzed enzymes are selected from the group consisting of a DNA repair enzyme, a poly(A) polymerase, a DNA end repair enzyme and a DNA A-tailing enzyme.

In embodiments, the protein may be fused to a substrate binding moiety and may be immobilized on a surface. The protein may be lyophilized. In another embodiment, a nucleic acid is provided that encodes the protein described above.

In embodiments, a method is provided that includes: (a) incubating a reaction mixture comprising a proteinase, a first enzyme, and a nucleic acid substrate for the first enzyme where the incubating is optionally for a period of time selected from 5-40 minutes, at a temperature selected from 4° C.-40° C. such that the proteinase proteolytically cleaves the first enzyme. The proteinase may be characterized by an amino acid sequence that is at least 90% identical to SEQ ID NO:1; and at least one amino acid substitution in a region of helix 3 corresponding to amino acids 225-240 of SEQ ID NO:1; and (b) the temperature of the reaction mixture is increased to a temperature of at least 50° C. (e.g. at least 60° C. or 65° C.). In some embodiments, step (b) comprises incubating the reaction mixture at the temperature for 5-40 minutes, such as for 10-20 minutes, or about 15 minutes.

The proteinase used in embodiments of the method has the properties of any of the embodiments of the protein described above.

In some embodiments, the method further includes (c) adding a second enzyme to the reaction mix after step (b), wherein the second enzyme modifies the nucleic acid substrate to produce a reaction product.

In examples of the method, the first enzyme may be selected from the group consisting of a polymerase, a ligase, an endonuclease, a deaminase, a kinase, and a DNA cleaving enzyme, or any combination thereof. Where the nucleic acid substrate is RNA, a first enzyme may be a poly (A) polymerase.

Where the nucleic acid substrate is DNA, the first enzyme may be one or more end-repair enzyme that blunts and, optionally, 5' phosphorylates DNA. Other examples of the nucleic acid substrate include Formalin-fixed Paraffin-Embedded (FFPE) DNA and the first enzyme is one or more DNA repair enzymes.

An example of a second enzyme includes a ligase for ligating adapters to the DNA, after step (b). Another example of a second enzyme includes enzymes for adding an A-tail to the DNA, after (b).

In some embodiments, the nucleic acid substrate may be DNA and the method further comprises: (c) adding additional enzyme to the reaction mix to A-tail the DNA, after (b).

In an embodiment, a kit is provided that contains any of the proteins described above wherein the protein is in solution in a storage vessel, is lyophilized, or is immobilized on a solid substrate. In some examples, the kit may provide in a separate tube, a first enzyme for combining with a nucleic acid substrate and when the reaction is complete adding the composition from the second tube to the mixture.

BRIEF DESCRIPTION OF THE FIGURES

The skilled artisan will understand that the drawings described below, are for illustration purposes only. The drawings are not intended to limit the scope of the present teaching in any way.

FIG. 3A to FIG. 3F shows that a Proteinase K variant having a substitution at position 236 of SEQ ID NO:1 can be inactivated after a 15-minute heat treatment at 60° C. compared to Proteinase K variants (other than the ones disclosed herein) and to the wild type enzyme under the same reaction conditions. In combination with other substitutions, this enzyme is completely inactivated at 50° C.

FIG. 3A shows that wild type Proteinase K is not inactivated at 4° C., 55° C., 60° C. or 65° C. The enzyme is fully active after heat treatment for all time periods and at all temperatures shown above 4° C.

FIG. 3B shows that the introduction of substitutions in a Proteinase K variant at positions 242, 247, and 265 of SEQ ID NO:1 enhances thermolability relative to the wild type Proteinase K. This enzyme is largely but not completely inactive after heat treatment at 60° C.

FIG. 3C shows that a Proteinase K having substitutions at positions 77, 147, 203, 242, and 265 of SEQ ID NO:1 displays enhanced thermolability at temperatures of 60° C. or above where the enzyme is largely but not completely inactivated after heat treatment at 60° C.

FIG. 3D shows a Proteinase K variant having a substitution at position 236 of SEQ ID NO:1 displays enhanced thermolability at 55° C. No activity is detected after heat treatment at 60° C. and 65° C.

FIG. 3E shows that a Proteinase K variant (2YH) that has a combination of a single substitution at position 236 and further substitutions at positions 242, 247, and 265 of SEQ ID NO:1. This enzyme is inactive after heat treatment at 50° C., 55° C., 60° C. and 65° C.

FIG. 3F shows that a Proteinase K variant (16YH) that has a combination of a single substitution at position 236 and further substitutions at positions 77, 147, 203, 242, and 265 of SEQ ID NO:1 has greatly enhanced thermolability. The variant is largely inactive at 50° C., with no activity detected after heat treatment at 55° C., 60° C. and 65° C.

FIG. 5A illustrates a workflow for library preparation and sequencing of FFPE DNA using a thermolabile Proteinase K to digest the DNA repair enzymes, after the DNA has been repaired and before A-tailing and ligation.

FIG. 5B illustrates that performing the workflow of FIG. 5A using beads to remove the repair enzymes instead of a thermolabile Proteinase K variant results in the formation of adaptor dimers.

FIG. 5C illustrates that performing the workflow of FIG. 5A using a thermolabile Proteinase K variant resulted in no detectable adapter dimer formation.

FIG. 6A shows a workflow for sequencing RNA using the Oxford Nanopore sequencing platform in which the first step (which uses beads to remove contaminant proteins) is replaced by a treatment with a thermolabile proteinase. Replacement of the separation step with a thermolabile proteinase treatment reduces loss of sample, which means that less sample need to be sequenced thereby reducing the cost of reagents. The first bead step in this method accounts for more than 50% sample loss.

FIG. 6B presents data in a histogram showing the loss of RNA after poly(A) tailing using bead purification and thermolabile Proteinase K treatment.

FIG. 7A shows a workflow for processing a DNA sample for sequencing using the Illumina sequencing platform in which the A-tailing reaction, which is normally terminated at 65° C., can be performed at 37° C. if a thermolabile proteinase is used to inactivate the enzymes prior to and after the A-tailing reaction. The use of a thermolabile proteinase in this method has the benefit of removing GC bias during sample preparation.

FIG. 7B shows the improvement in library yield by Illumina sequencing using the workflow in FIG. 7A. "Ultra II" is intended to encompass the standard NEBNext® protocol (New England Biolabs, Ipswich, Mass.) without Proteinase K.

FIG. 7C shows that the use of a thermolabile proteinase significantly improves sequence coverage of the high AT-content regions of human genome when used in the workflow shown in in FIG. 7A. The GC-bias curves from duplicate libraries made using the NEBNext Ultra II DNA Library Prep Kit for Illumina (Ultra II-1 and Ultra II-2) (New England Biolabs, Ipswich, Mass.) were compared with data from duplicate libraries generated by the protocol utilizing thermolabile Proteinase K (Proteinase K-1 and Proteinase K-2).

FIG. 8A-FIG. 8F show the increased thermolability of Proteinase K variants compared to the wild type at various temperatures ranging from 50° C. to 65° C.

FIG. 8A shows the sequences of the hydrophobic core 230-237. within helix 3 (amino acid residues 225-240) of wild type Proteinase K and Proteinase K variants where each of 19 amino acids were substituted at a position corresponding to position 236 of SEQ ID NO:1 and were found to increase thermolability.

FIG. 8B shows that individually substituting tyrosine at position 236 with glutamine (Q), lysine (K), glutamate (E), arginine (R) or glycine (G) results in a Proteinase K variant with enhanced thermolability relative to wild type Proteinase K.

FIG. 8C shows that individually substituting tyrosine at position 236 with histidine (H), phenylalanine (F), valine (V), aspartate (D) or threonine (T) results in a Proteinase K variant with enhanced thermolability relative to wild type Proteinase K.

FIG. 8D shows that individually substituting tyrosine at position 236 with leucine (L), isoleucine (I), methionine (M), serine (S) or tryptophan (W) results in a Proteinase K variant with enhanced thermolability relative to wild type Proteinase K.

FIG. 8E shows that individually substituting tyrosine at position 236 with proline (P) abolishes Proteinase K activity. Individually substituting tyrosine at position 236 with alanine (A), asparagine (N) or cysteine (C) results in a Proteinase K variant with enhanced thermolability relative to wild type Proteinase K.

FIG. 8F shows that individually mutating other positions within helix 3 (V230T and L233N) results in a Proteinase K variant with enhanced thermolability relative to wild type Proteinase K.

DETAILED DESCRIPTION OF EMBODIMENTS

Figure 1:
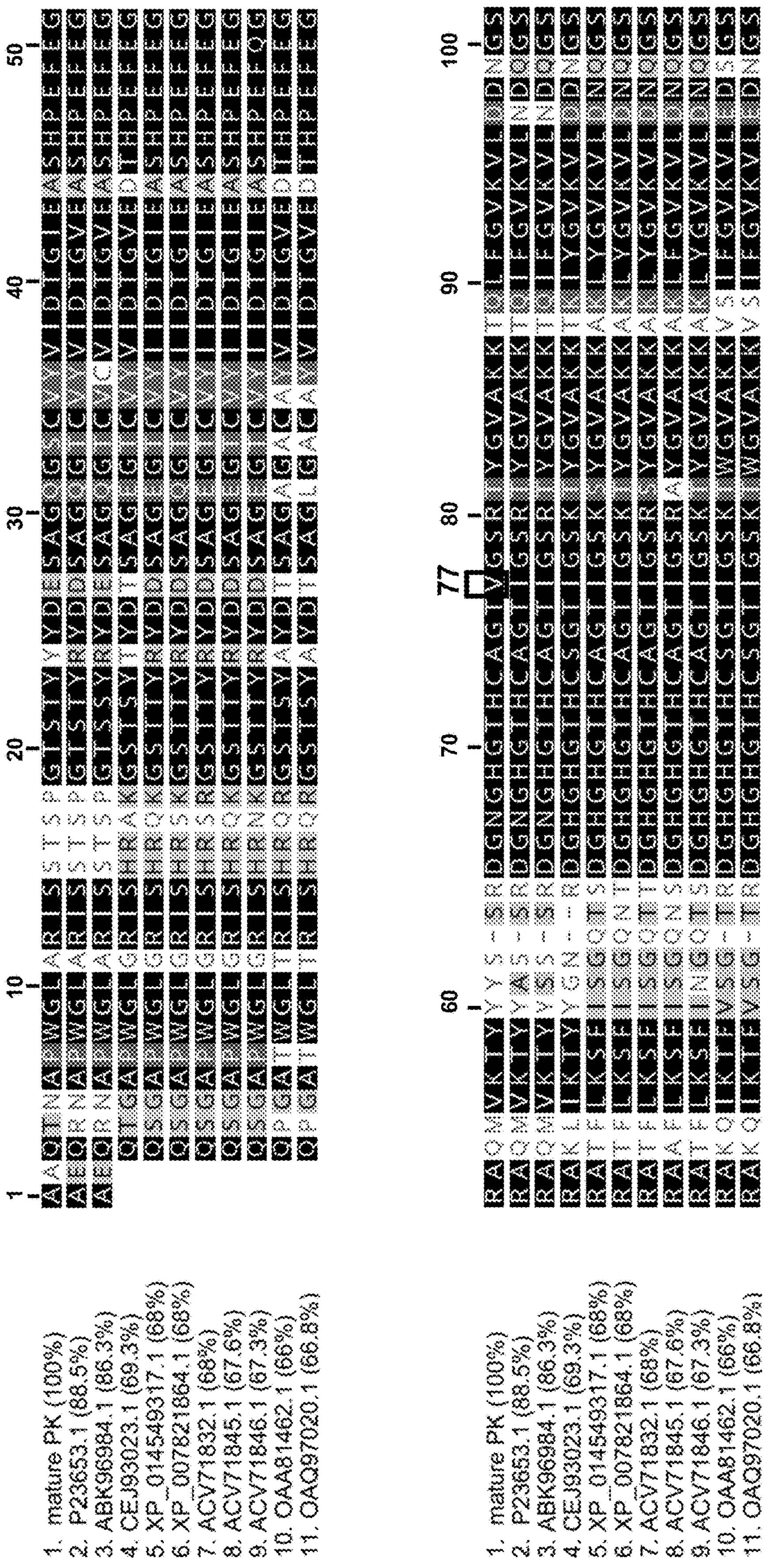
FIG. 1 shows the alignment of the wild type Proteinase K from *Engyodontium album* (SEQ ID NO:1) with 10 different serine proteases that are also endopeptidases and share at least 66% sequence identity with SEQ ID NO:1. SEQ ID NOs:2-11 are sequences deposited in GenBank and identified in a BLAST search of the Genbank database and are associated with an accession number (Swiss-Prot or GenBank). SEQ ID NO:1: see GenBank P06873.2 starting at amino acid 106 which is the first amino acid of the mature form of Proteinase K; SEQ ID NO:2: see Genbank Accession No. P23653.1 starting at amino acid 109 which is the first amino acid of the mature form of the protein; SEQ ID NO:3: see Genbank Accession No. ABK96984.1 starting at amino acid 109 which is the first amino acid of the mature form of the protein; SEQ ID NO:4: see Genbank Accession No. CEJ93023.1 1 starting at amino acid 111 which is the first amino acid of the mature form of the protein; SEQ ID NO:5: see Genbank Accession No. XP_014549317.1 starting at amino acid 112 which is the first amino acid of the mature form of the protein; SEQ ID NO: 6: see Genbank Accession No. XP_007821864.1 starting at amino acid 112 which is the first amino acid of the mature form of the protein; SEQ ID NO:7: see Genbank Accession No. ACV71832.1 starting at amino acid 112 which is the first amino acid of the mature form of the protein; SEQ ID NO:8: see Genbank Accession No. ACV71845.1 starting at amino acid 112 which is the first amino acid of the mature form of the protein; SEQ ID NO: 9: see Genbank Accession No. ACV71846.1 starting at amino acid 112 which is the first amino acid of the mature form of the protein; SEQ ID NO: 10: see Genbank Accession No. OAA81462.1 starting at amino acid 94 which is the first amino acid of the mature form of the protein; and SEQ ID NO: 11: see Genbank Accession No. OAQ97020.1 starting at amino acid 109 which is the first amino acid of the mature form of the protein.
Figure 1:
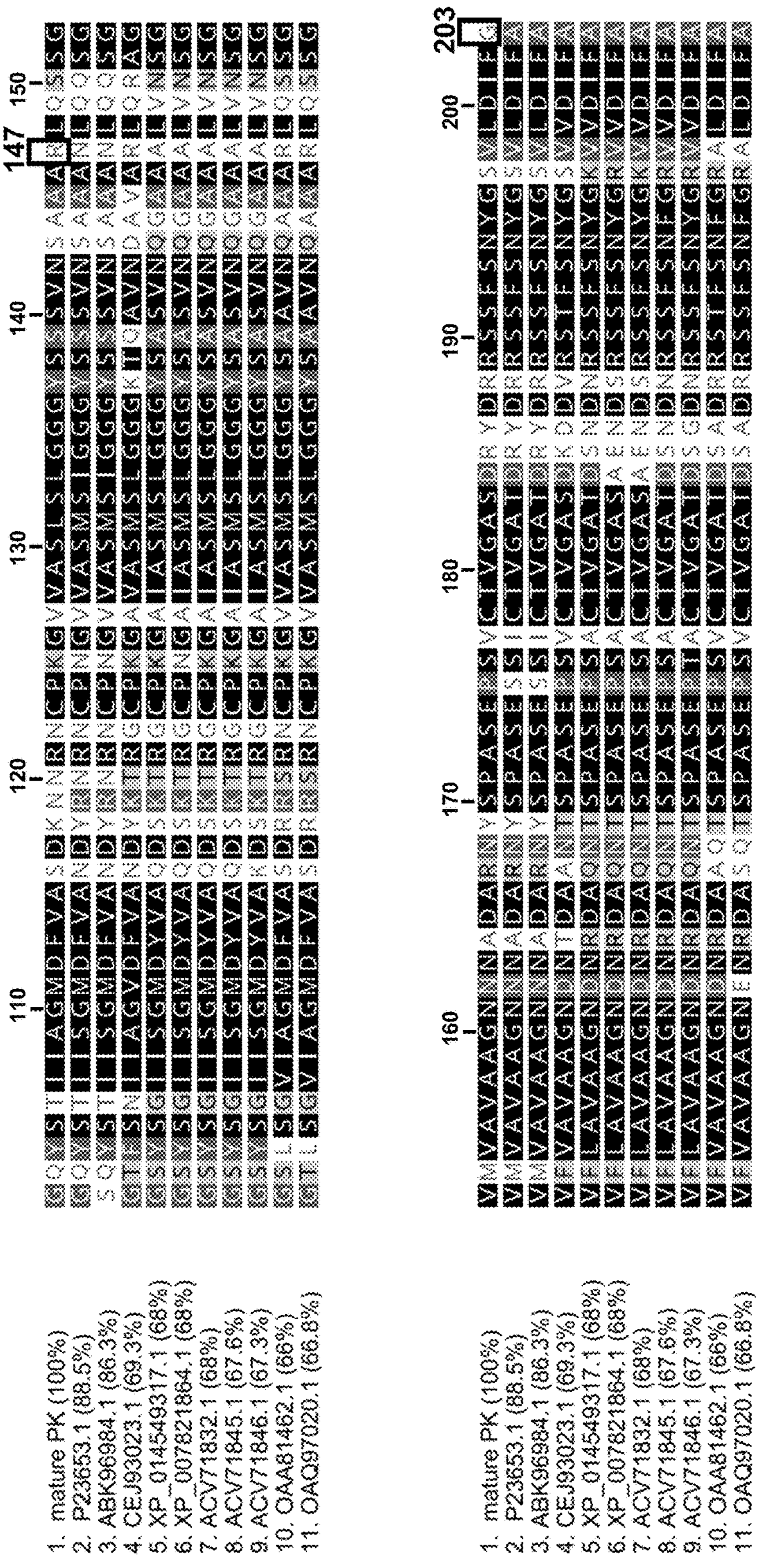
Figure 1:
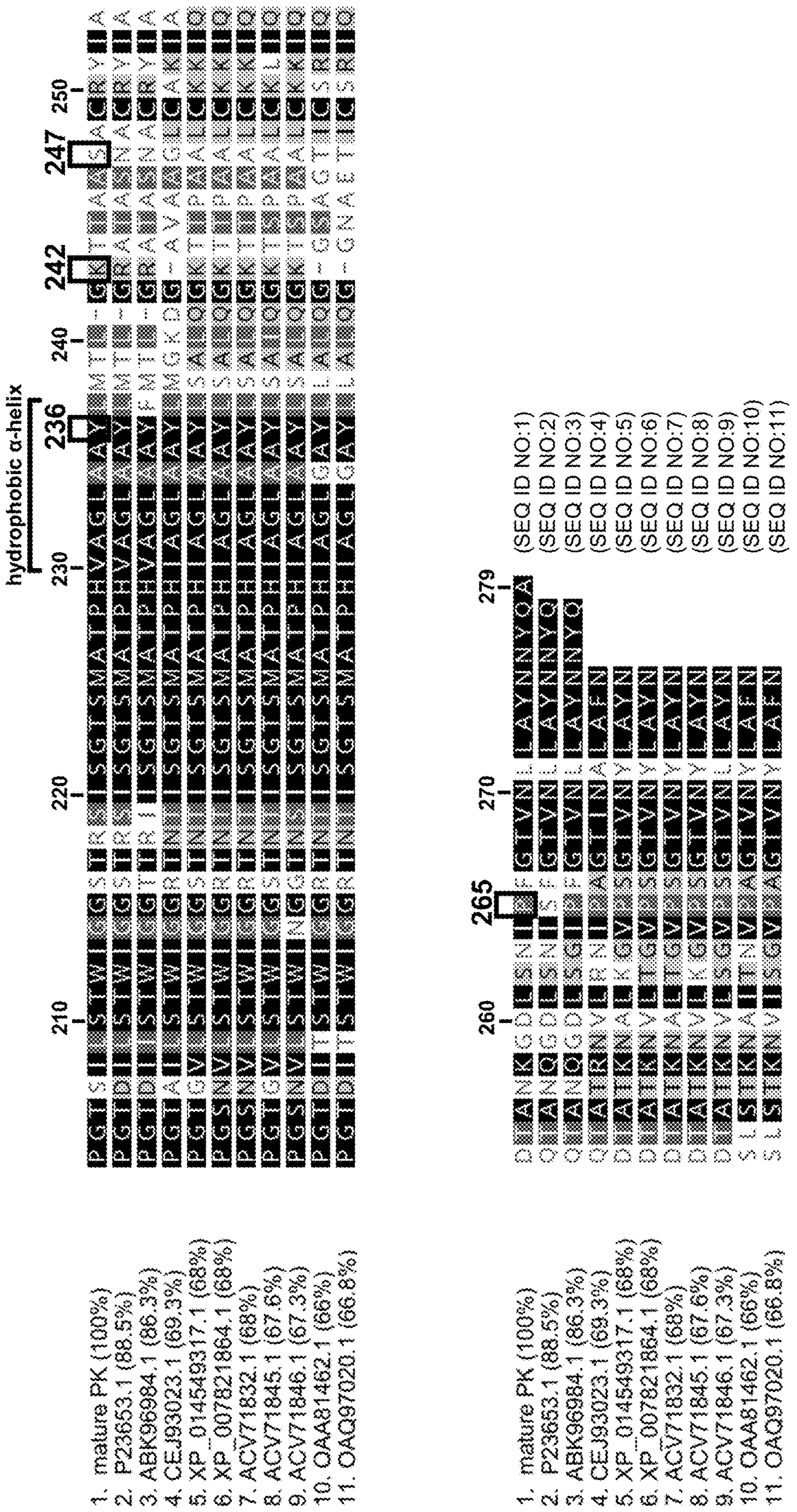
Figure 2:
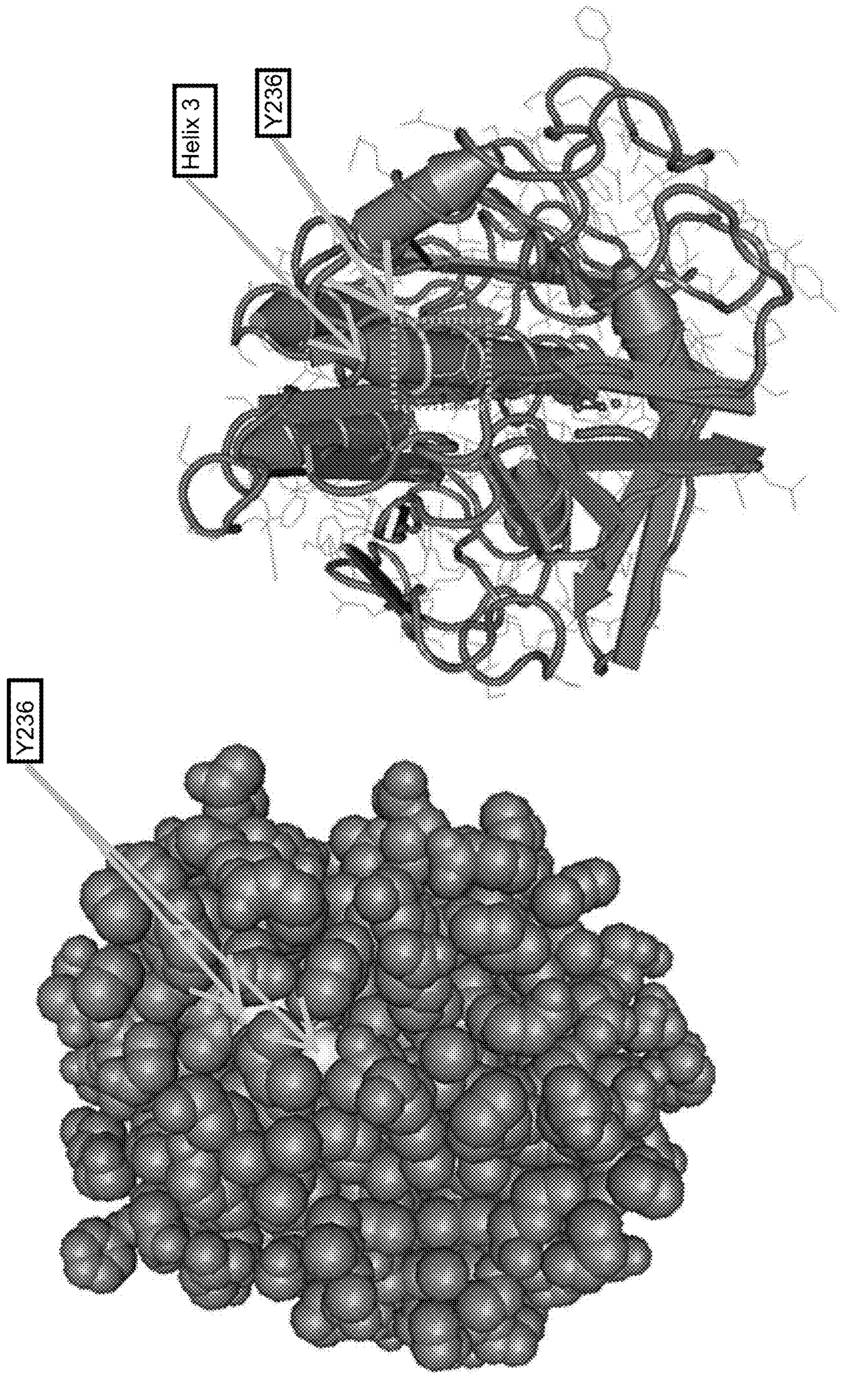
FIG. 2 shows the 3-dimensional structure of Proteinase K with a central alpha-helical region indicated as a grey cylinder. This hydrophobic region is referred to as helix 3 and is labelled accordingly spanning a region corresponding to 225-240 in SEQ ID NO:1 which is buried inside Proteinase K.

The present disclosure relates to proteinase variants and their uses.

The term "thermolability" or "thermolabile" as used herein refers to the feature of heat sensitivity of the protease activity of a proteinase variant compared with the activity of the wild type proteinase under similar conditions of time and temperature. For example, a proteinase variant having a substitution in helix 3 (corresponding to amino acid residues 230-237 of SEQ ID NO:1) may be determined to be thermolabile by measuring the heat sensitivity of the proteinase variant enzyme activity. This can be achieved by heat treating a proteinase variant for a selected period of time (for example, for 5-40 minutes, such as for at least 5 minutes, 10 minutes, 15 minutes, and for up to about 20 minutes, 30 minutes or 40 minutes; typically for about 15 minutes) and at various temperatures from 4° C. to 50° C. or above (such as at about 55° C., 60° C. or 65° C.) and then combining the heat treated enzyme with a substrate polypeptide at a standard reaction temperature (for example at 37° C.) to determine its proteolytic activity or the loss of proteolytic activity. Thermolability of a proteinase variant may be observed when compared with a wild type proteinase such as wild type Proteinase K. A proteinase may be referred to as having increased thermolability relative to a reference enzyme (e.g., a wild type proteinase or another variant proteinase) if (a) it loses a higher percentage of its proteolytic activity when exposed to the same conditions as the reference enzyme (e.g. loss of 90% of activity upon exposure to 60° C. for 15 minutes compared to a reference enzyme that loses only 70% of its activity upon exposure to 60° C. for 15 minutes); (b) it loses the same percentage of its proteolytic activity as the reference enzyme but upon exposure to a lower temperature than the reference enzyme (e.g., loss of 90% of activity upon exposure to 55° C. for 15 minutes compared to a reference enzyme that loses 90% of its activity upon exposure to 75° C. for 15 minutes); or (c) it loses the same percentage of its proteolytic activity as the reference enzyme in a shorter time than the reference enzyme at the same temperature (e.g., loss of 90% of activity upon exposure to 60° C. for 5 minutes compared to another enzyme that loses 90% of its activity upon exposure to 60° C. for 15 minutes).

The term "inactive" or "inactivated" as used herein refers to an enzyme that has lost at least 90%, at least 95%, least 98%, at least 99%, or 100% of its activity.

The term "corresponding to" in the context of corresponding positions as used herein, refers to positions that lie across from one another when sequences are aligned, for example, by the BLAST algorithm. An amino acid position that is mutated by substitution, deletion or addition in one wild type proteinase sequence can be used to identify an amino acid substitution, deletion, or addition at the corresponding position in another different wild type proteinase sequence by alignment of the protein sequences. Similarly, an amino acid position in one proteinase may correspond to a position within a functionally equivalent motif or structural motif that can be identified within one or more other proteinase(s) in a database by alignment of the motifs.

The term "hydrophobic" residues as used herein refer to non-polar aliphatic and aromatic R groups (side chains). These include glycine (G), alanine (A), valine (V), leucine (L), isoleucine (I), phenylalanine (F), tyrosine (Y) and tryptophan (W).

The term "non-hydrophobic" residues as used herein refer to polar uncharged, negatively charged, and positively charged R groups. This group includes serine (S), threonine (T), cysteine(C), methionine (M), asparagine (N), glutamine (Q), aspartate (D), glutamate (E), lysine (K), arginine (R), and histidine (H). This group as here described also includes proline (P).

The term "proteolyzed enzyme" as used herein refers to an enzyme that has been degraded by the proteolytic activity of another enzyme. The term "proteolytic" describes the activity of a protease, for example, a serine protease or an endopeptidase such as from the peptidase family S8 exemplified of SEQ ID NOs:1-11.

The term "proteinase" as used herein refers to any endopeptidase that hydrolyzes peptide bonds between non-terminal amino acids. A proteinase may be described as having proteinase, protease or proteolytic activity. These terms can be used interchangeably to describe the activity of a proteinase. Proteinases reveal certain conserved sequences which are common to this family of enzymes. The preferred embodiment is a Proteinase K variant because not only can this variant be mutated to be thermolabile as can other members of the family, but it also retains a high level of proteolytic activity at the preferred temperature of activity (4° C.-40° C.). Wherever the term "proteinase variant" is used, this is intended to include proteinases related by sequence as specified.

The term "non-naturally occurring" as used herein refers to a composition that does not exist in nature. A "non-naturally occurring" protein may have an amino acid sequence that is different from a naturally occurring amino acid sequence for example, one or more amino acid substitutions, deletions or insertions at the N-terminus, the C-terminus and/or between the N- and C-termini of the protein. Hence the non-naturally occurring protein may have less than 100% sequence identity to the amino acid sequence of a naturally occurring protein although it may have at least 80%, at least 85%, at least 90%, at least 95%, at least 97%, at least 98%, at least 98.5% or at least 99% identity to the naturally occurring amino acid sequence. In certain cases, a non-naturally occurring protein may include a protein that has a post-translational modification pattern that is different from the protein in its natural state for example, an N-terminal methionine or may lack one or more post-translational modifications (e.g., glycosylation, 5 phosphorylation, etc.) if it is produced by a different (e.g., bacterial) cell.

In the context of a nucleic acid, the term "non-naturally occurring" refers to a nucleic acid that contains: a) a sequence of nucleotides that is different from a nucleic acid in its natural state (i.e., having less than 100% sequence identity to a naturally occurring nucleic acid sequence); b) one or more non-naturally occurring nucleotide monomers (which may result in a non-natural backbone or sugar that is not G, A, T or C); and/or c) may contain one or more other modifications (e.g., an added label or other moiety) to the 5'-end, the 3' end, and/or between the 5'- and 3'-ends of the nucleic acid.

In the context of a composition, the term "non-naturally occurring" refers to: (a) a combination of components that are not combined by nature, e.g., because they are at different locations, in different cells or different cell compartments; (b) a combination of components that have relative concentrations that are not found in nature; (c) a combination that lacks something that is usually associated with one of the components in nature; (d) a combination that is in a form that is not found in nature, e.g., dried, freeze dried, crystalline, aqueous; and/or (e) a combination that contains a component that is not found in nature. For example, a composition may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature. The non-naturally occurring polymerase may be purified so that it does not contain DNases, RNases or other proteins with undesirable enzyme activity or undesirable small molecules that could adversely affect the sample substrate or reaction kinetics.

As used herein and in the appended claims, the singular forms "a", "an", and "the" include plural referents unless the context clearly dictates otherwise. For example, the term "a protein" refers to one or more protein, i.e., a single protein and multiple proteins. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

Proteinase K is a robust enzyme that is used as a reagent to digest proteins. Proteinase K is thus a useful enzyme for purification of nucleic acids from lysates. Once digestion has been completed, it is often necessary to remove the enzyme so that it does not digest reagent enzymes added subsequently to the nucleic acid reaction for further nucleic acid processing and analysis. Thermolability obviates the need to remove the enzyme. By raising the temperature of the reaction mix, the proteinase variants described herein can be substantially or completely inactivated.

Proteinase K is a broad-spectrum protease that is widely used in molecular biology applications. Protein engineering has been used to enhance the protein activity (Liao et al. BMC Biotechnology 2007, 7:16). Other wild type proteases have been investigated for their proteolytic properties and their heat sensitivity (see Moran, et al. FEMS Microbiology Letters 197 (2001) 59-63 and ArcticZymes® Proteinase (ArcticZymes, Norway). The wild type amino acid sequences for 11 isolates of proteinases have been aligned and the alignment is shown in FIG. 1. The aligned amino acid sequences are for mature proteinases. For example, wild type Proteinase K from *Engyodontium album* (SEQ ID NO:1) does not include the signal peptide (15 amino acids) and the propeptide (90 amino acids). Thus, the amino acid sequence for wild type Proteinase K is numbered 1-279 where amino acid 1 corresponds to amino acid 106 of the amino acids encoded by the gene for the wild type Proteinase K.

Wild type Proteinase K comprises a hydrophobic alpha helix (also referred to as "Helix 3"). The helix 3 sequence is located at amino acid residues 230-237 of SEQ ID NO:1, and at corresponding positions in each of SEQ ID NOs:2-11. The wild-type helix 3 sequence is exemplified by the amino acid sequence VAGLAAYL (SEQ ID NO:12).

Figure 4:
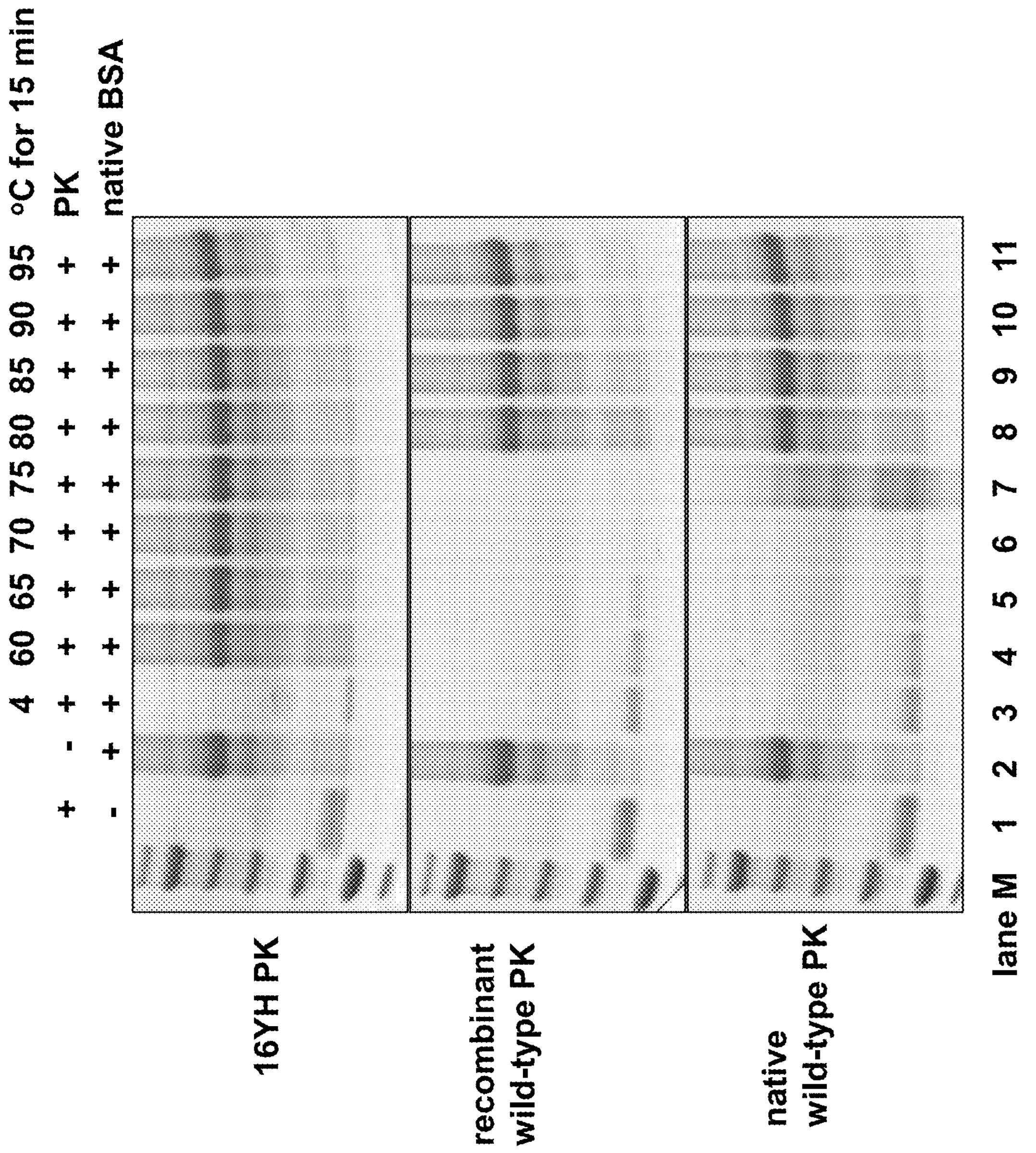
FIG. 4 shows that a Proteinase K variant (16YH) has no detectable proteinase activity after heat treatment at temperatures tested above 4° C., as determined using a gel assay in which the presence or absence of intact bovine serum albumin substrate is determined. In contrast, wild type or recombinant wild type Proteinase K remained active and completely digested the BSA after heat treatment at all the tested temperatures between 4° C. and 75° C.

The activity of wild type Proteinase K persists even after exposure to high temperatures (see for example FIG. 4 where Proteinase K digestion of proteins is observed after exposure to 75° C. for 15 minutes). Consequently, although this protease may be used in the purification of nucleic acids to digest unwanted proteins, its proteolytic activity would linger and inactivate enzymes used downstream in nucleic acid analysis with negative consequences for subsequent reactions.

In contrast, proteinase variants having substitutions in helix 3 (which corresponds to amino acids 230-237 of SEQ ID NO:1) have increased thermolability, without significantly affecting protease activity at a desired reaction temperature.

For example, a proteinase variant may have at least about 80%, 85%, 90% or 95% of the protease activity of an equivalent amount of wild type Proteinase K prior to either one being exposed to an elevated temperature (e.g. 65° C.), but the thermolabile variant may have less than 10%, 8%, 6% or 5% protease activity of the wild type Proteinase K when or after both are exposed to the same elevated temperature (e.g. 65° C.). For example, a thermolabile proteinase variant having at least 80% identity to SEQ ID NO:1 (but less than 100% sequence identity) and having any amino acid other than tyrosine at the position corresponding amino acid 236 of SEQ ID NO: 1 is inactivated after an incubation at 65° C. for 15 minutes (see for example, FIG. 8A-FIG. 8E).

Embodiments include multiple proteinase variants with the desired property of thermolability at temperatures in the range of 50° C.-65° C., for example, at 55° C.-65° C. or at 60° C.-65° C., resulting in a substantial degree of inactivation of protease activity. Thermolability with associated inactivation of protease activity can be achieved after incubation periods of preferably no more than 40 minutes, more particularly no more than 30 minutes or no more than 20 minutes. Inactivation of the proteinase variants may be achieved in as little as 5 minutes and hence incubation times at the aforementioned temperatures may also be as little as 5 minutes. The extent of loss of protease activity, can be measured by analyzing the degradation of a protein or peptide substrate such as described in Example 1 under selected conditions of temperature and time.

Embodiments of thermolabile proteinase variants include variants in which one or more amino acids (e.g., two, three four, five, six, seven or all eight of the amino acids) within the hydrophobic alpha helix (also referred to as Helix 3) exemplified by VAGLAAYL (SEQ ID NO:12) corresponding to positions 230-237 of SEQ ID NO:1, and for other proteinases defined by SEQ ID NOs:2-11 at positions corresponding to positions 230-237 of SEQ ID NO:1. Optionally additional substitutions of amino acids outside the helix 3 motif may further increase thermolability.

Figure 8B:
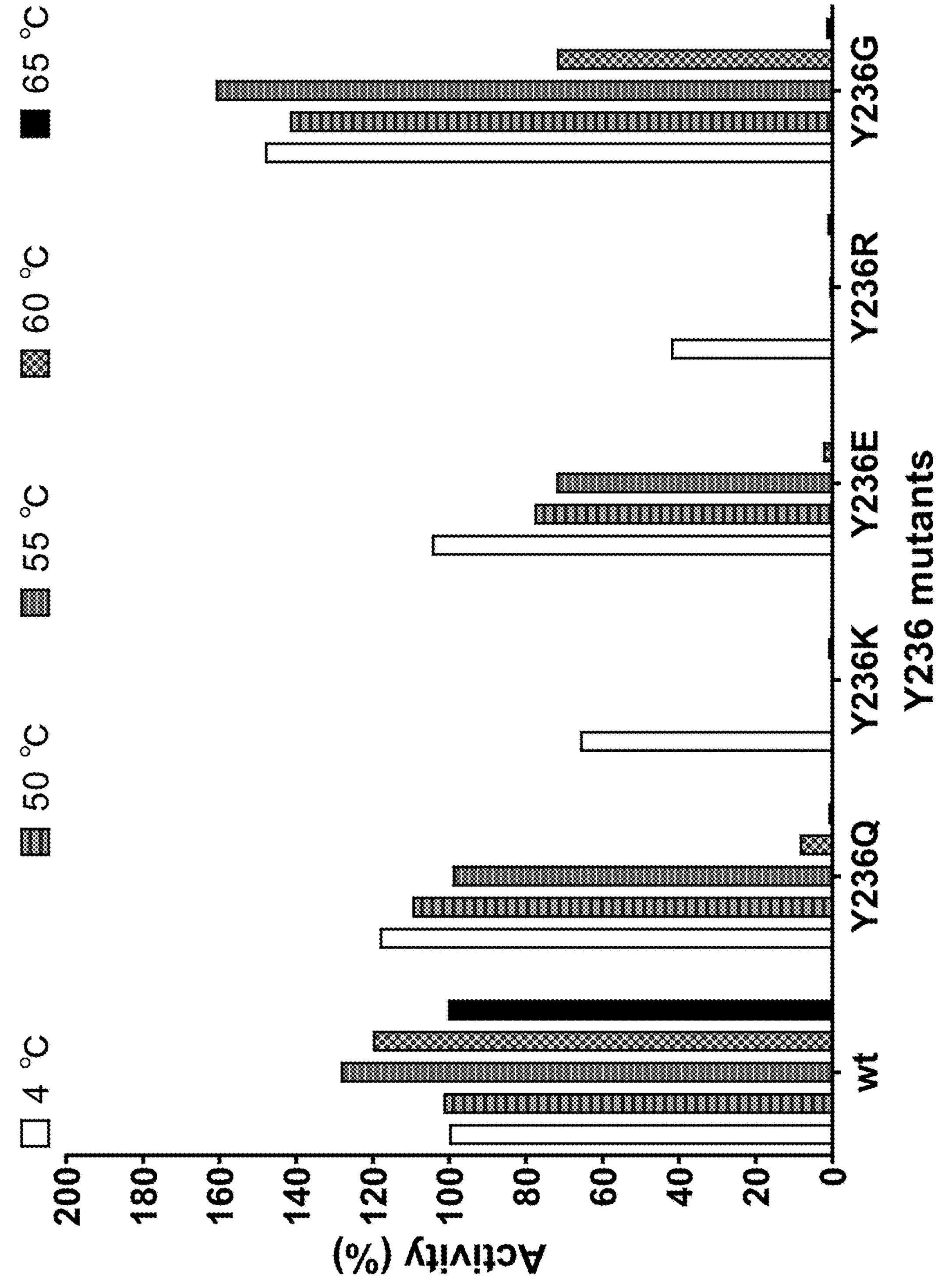
Figure 8C:
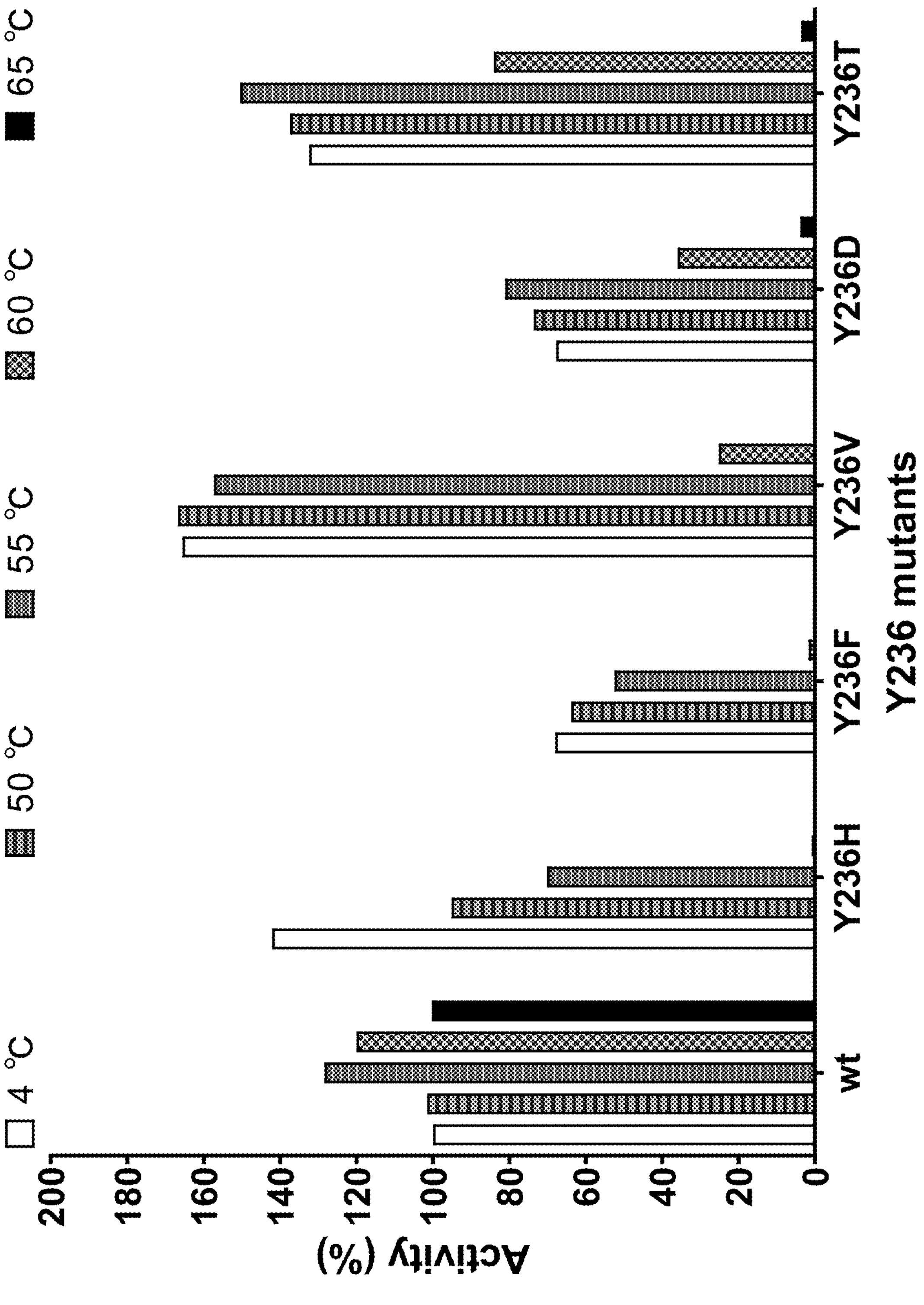
Figure 8D:
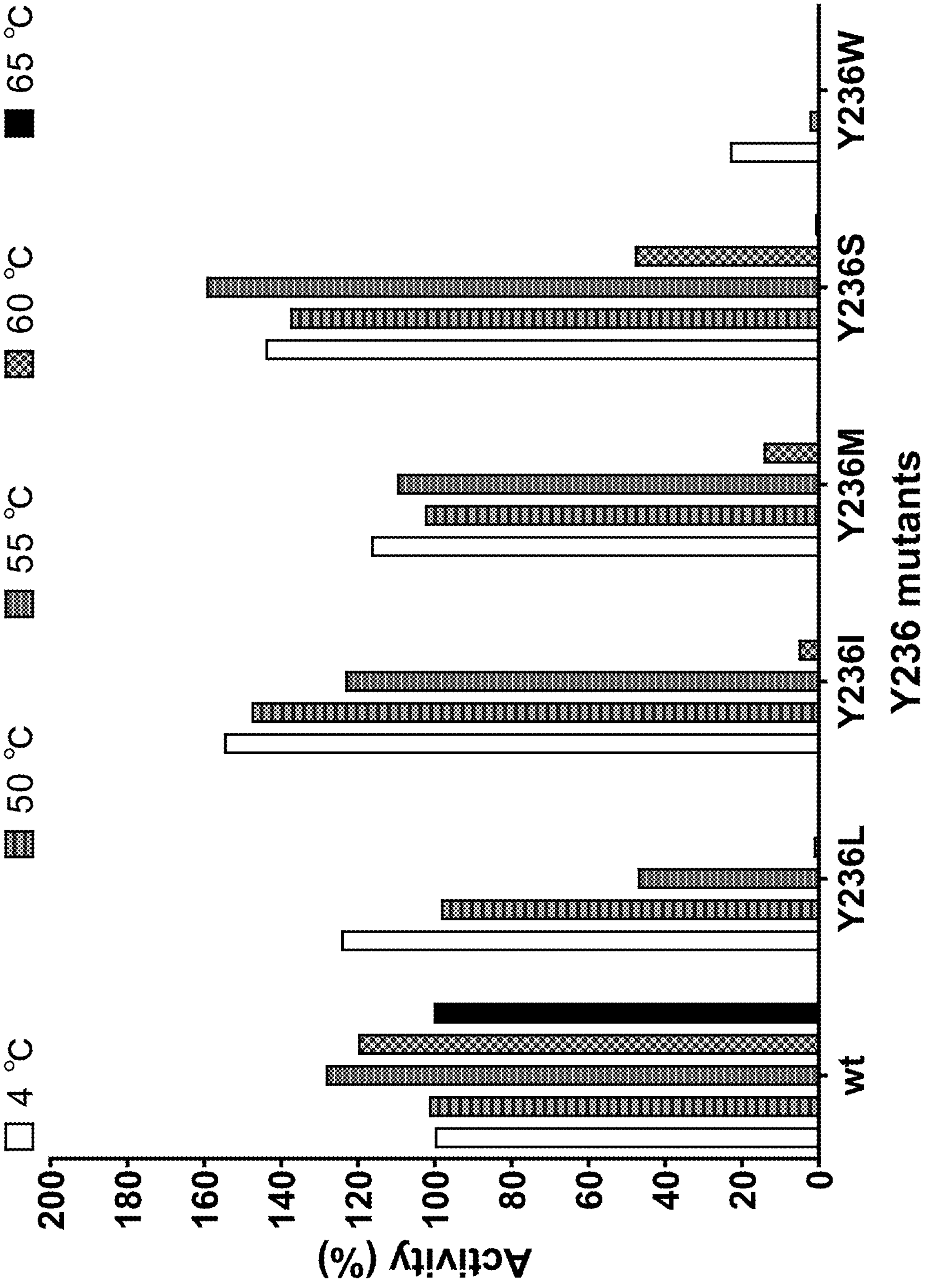
Figure 8E:
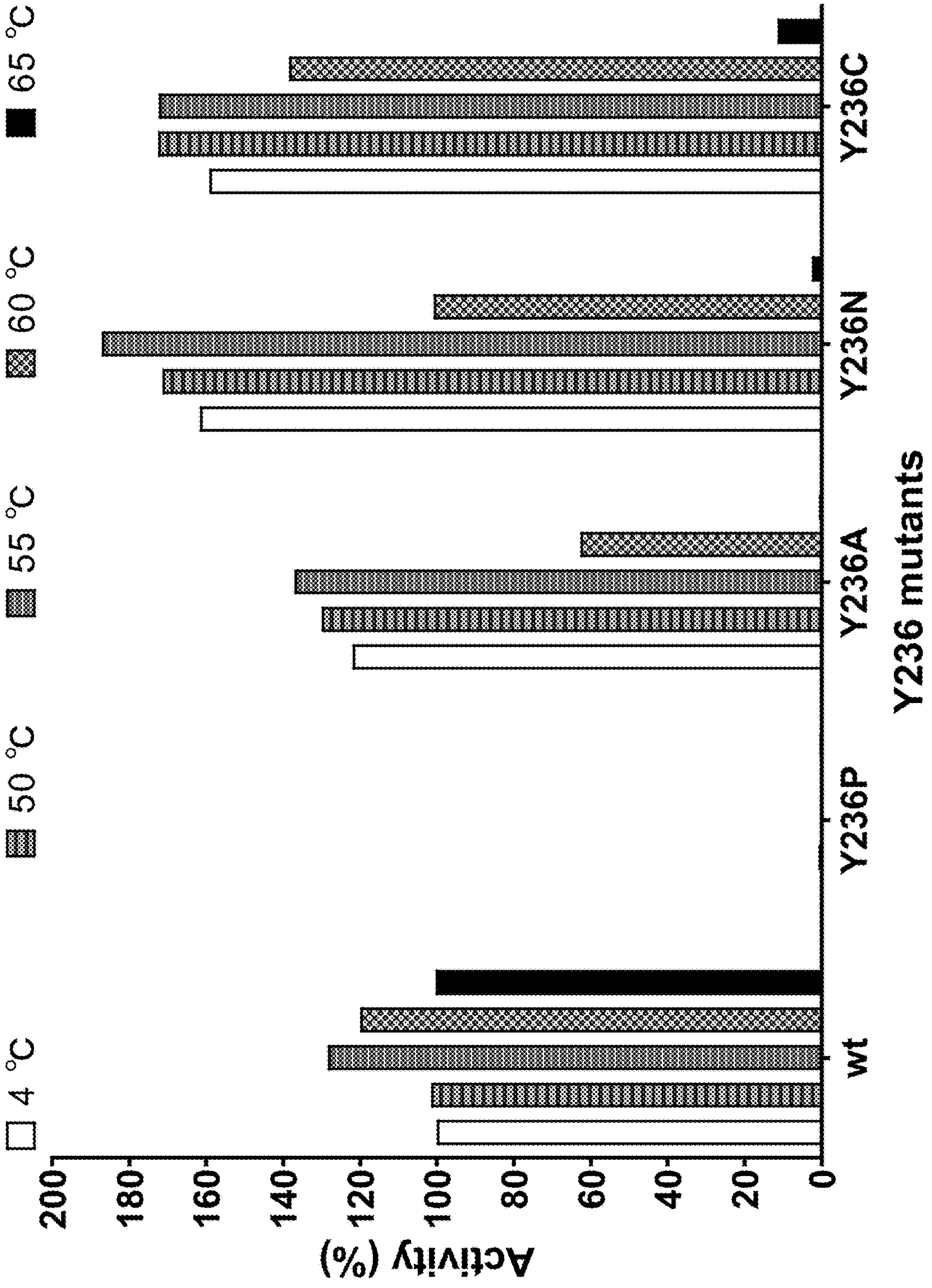
Figure 8F:
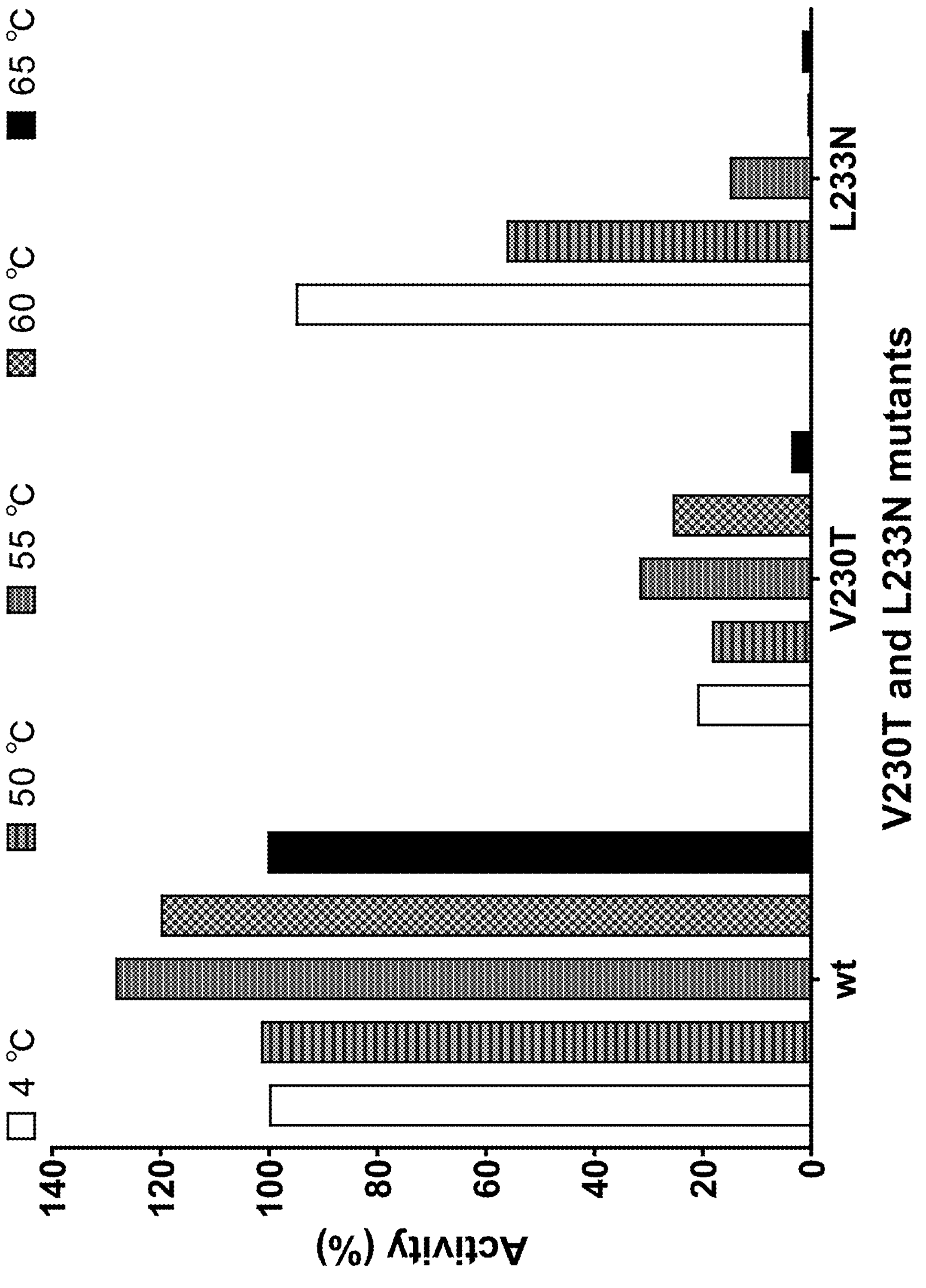

Examples of substitutions in helix 3 are provided in FIG. 8A. Changes in this region were found to significantly reduce the stability of the enzyme at elevated temperatures so that the proteinase variants were inactivated by temperatures at which the wild type Proteinase K enzyme is fully active (FIG. 8B-FIG. 8F). Despite having increased thermolability, proteinase variants (i.e., with no prior exposure to elevated temperatures) have the desired protease activity at standard reaction temperatures.

For example, tyrosine at position 236 (of SEQ ID NO:1), which has a large hydrophobic side chain, may be changed to any other amino acid. As exemplified in FIG. 8C for SEQ ID NO:1, Proteinase K variants having a Y236H substitution display significant loss of proteolytic activity when exposed to temperatures above 55° C. Y236V has proteinase activity that is greater than wild type Proteinase K after exposure to temperatures up to 55° C. At 60° C. the proteolytic activity of the Y236V variant is significantly reduced and is undetectable at 65° C. A similar pattern is seen not only by substituting other amino acids at the same position, but also making substitutions in other positions within helix 3 (FIG. 8A-FIG. 8F).

In some embodiments, the substitution at the position corresponding to 236 of SEQ ID NO:1 is selected from the group of amino acids that do not have hydrophobic aromatic side chains.

In some embodiments, the substitution at the position corresponding to 236 of SEQ ID NO:1 is selected from the group of amino acids that are not hydrophobic.

A proteinase variant may (a) have an amino acid sequence that is at least 80%, 85%, 90% or 95% identical to any of SEQ ID NO: 1-11 (but less than 100% identity to any of SEQ ID NOs: 1-11); (b) at least one amino acid substitution in helix 3 corresponding to amino acids 230-237 of SEQ ID NO:1 (V230, A231, G232, L233, A234, A235, Y236 and L237), wherein the substitution is not isoleucine (I) at a position corresponding to position 230 of SEQ ID NO:1, wherein the substitution is not glycine (G) at a position corresponding to position 231, 234 or 235 of SEQ ID NO:1 and wherein the substitution is not phenylalanine (F) at a position corresponding to position 237 of SEQ ID NO:1; and (c) optionally have an additional amino acid substitution in the position corresponding to any one or more of V77, R147, G203, A226, T227, P228, H229, M238, T239, L240, K242, 5247, or P265 of SEQ ID NO: 1 (such as at any 2, 3, 4, 5, 6, 7, 8, 9, 10, 11, 12 or all 13 of these positions). In some embodiments, a proteinase variant may have (a) an amino acid sequence that is at least 90% identical to SEQ ID NO: 1 (but less than 100% identity) and; (b) at least one amino acid substitution in helix 3 corresponding to amino acids 230-237 of SEQ ID NO:1 (V230, A231, G232, L233, A234, A235, Y236 and L237), wherein the substitution is not isoleucine (I) at a position corresponding to position 230 of SEQ ID NO:1, wherein the substitution is not glycine (G) at a position corresponding to position 231, 234 or 235 of SEQ ID NO:1 and wherein the substitution is not phenylalanine (F) at a position corresponding to position 237 of SEQ ID NO:1; and (c) optionally have an additional amino acid substitution in the position corresponding to any one or more of V77, R147, G203, A226, T227, P228, H229, M238, T239, L240, K242, S247, or P265 of SEQ ID NO:1 (such as at any 2, 3, 4, 5, 6, 7, 8, 9, 10, 11, 12 or all 13 of these positions).

Exemplary amino acid substitutions that can be made in the hydrophobic alpha helix (helix 3) of a protease that has at least 80% or 90% sequence identity to any of SEQ ID NOs:1-11 are listed below:

The valine corresponding to position 230 of SEQ ID NO:1 may be substituted by any amino acid except for isoleucine (I), i.e., serine, threonine, cysteine, methionine, proline, asparagine, glutamine, aspartate, glutamate, lysine, arginine, histidine, glycine, alanine, leucine, tryptophan, tyrosine, or phenylalanine.

The alanine corresponding to position 231 of SEQ ID NO:1 may be substituted by any amino acid except for glycine, i.e., serine, threonine, cysteine, methionine, proline, asparagine, glutamine, aspartate, glutamate, lysine, arginine, histidine, valine, leucine, isoleucine, tryptophan, tyrosine, or phenylalanine.

The glycine corresponding to position 232 of SEQ ID NO:1 may be substituted by any amino acid, i.e., serine, threonine, cysteine, methionine, proline, asparagine, glutamine, aspartate, glutamate, lysine, arginine, histidine, alanine, valine, leucine, isoleucine, tryptophan, tyrosine, or phenylalanine.

The leucine corresponding to position 233 of SEQ ID NO:1 may be substituted by any amino acid, i.e., serine, threonine, cysteine, methionine, proline, asparagine, glutamine, aspartate, glutamate, lysine, arginine, histidine, glycine, alanine, valine, isoleucine, tryptophan, tyrosine, or phenylalanine.

The alanine corresponding to position 234 of SEQ ID NO:1 may be substituted by any amino acid except for glycine, i.e., serine, threonine, cysteine, methionine, proline, asparagine, glutamine, aspartate, glutamate, lysine, arginine, histidine, valine, leucine, isoleucine, tryptophan, tyrosine, or phenylalanine.

The alanine corresponding to position 235 of SEQ ID NO:1 may be substituted by any amino acid except for glycine, e.g., serine, threonine, cysteine, methionine, proline, asparagine, glutamine, aspartate, glutamate, lysine, arginine, histidine, valine, leucine, isoleucine, tryptophan, tyrosine, or phenylalanine.

The tyrosine corresponding to position 236 of SEQ ID NO:1 may be substituted by any amino acid, i.e., serine, threonine, cysteine, methionine, proline, asparagine, glutamine, aspartate, glutamate, lysine, arginine, histidine, glycine, valine, alanine, leucine, isoleucine, tryptophan, or phenylalanine.

The leucine corresponding to position 237 of SEQ ID NO:1 may be substituted by any amino acid except for phenylalanine, i.e., serine, threonine, cysteine, methionine, proline, asparagine, glutamine, aspartate, glutamate, lysine, arginine, histidine, glycine, alanine, valine, isoleucine, tryptophan, or tyrosine.

In one embodiment, the proteinase comprises an amino acid sequence that is at least 80% identical but less than 100% identical to any of SEQ ID NO:1, and has an amino acid substitution in helix 3 at position 236 of SEQ ID NO: 1 and further substitutions at positions 242, 247, and 265 of SEQ ID NO:1. In one embodiment, one or more of these substitutions (e.g. 2, 3, or all 4 of these substitutions) are selected from Y236H, K242R, S247N, and P265S.

In one embodiment, the proteinase comprises an amino acid sequence that is at least 80% identical but less than 100% identical to any of SEQ ID NO:1, and has an amino acid substitution in helix 3 at position 236 of SEQ ID NO:1 and further substitutions at positions 77, 147, 203, 242, and 265 of SEQ ID NO:1. In one embodiment, one or more of these substitutions (e.g. 2, 3, 4, 5, or all 6 of these substitutions) are selected from Y236H, V77I, R147N, G203A, K242R, and P265S.

A proteinase variant may be included in a variety of compositions. For example, a composition may comprise a proteinase variant and a media (e.g., an aqueous media, a solvent, a suspension agent). A composition may further comprise one or more proteins or peptides such as enzymes or proteolytic products arising from the activity of a proteinase variant), one or more salts, one or more buffers at a suitable pH within the range of pH2-pH12, one or more of any of adjuvants, carriers, nucleic acids, nucleotide phosphates, additives such as a detergent (anionic, cationionic, zwitterionic or non-charged) and stabilizing agents such as glycerol, BSA, DTT and EDTA. The proteinase variant described above may be in a DNA free and/or RNA free preparation as a reagent. The proteinase variant may have a shelf life in a buffer of at least one year or at least 2 years wherein the activity of the variant is not diminished or is diminished by no more than 10%. The temperature of storage may be at a temperature of at least one of room temperature, 4° C., −20° C. or −70° C.

A composition comprising the proteinase variant, or the purified proteinase variant may be formulated for use in a buffer or as an emulsion, a solid, granule, lyophilized state, gel, pellet, or powder. The variant may be immobilized on a solid surface such as a matrix, bead, paper, plastic, resin, column, chip, microfluidic device or other instrument platform where the proteinase variant adheres directly or via an affinity binding domain. The affinity binding domain may be covalently linked to the proteinase variant in the form of a fusion protein for example, maltose binding protein, chitin binding domain, His-tag, SNAP-tag® (New England Biolabs, Ipswich, Mass.) biotin etc. or may be non-covalently linked to a substrate using for example, an antibody.

Proteinase variants described herein were made using New England Biolabs (Ipswich, Mass.) reagents from synthesized genes (Integrated DNA Technologies, Coralville, Iowa). The synthesized genes were inserted into an expression vector and mutagenized using a mutagenesis kit. The vector encoding the mutagenized protein was then used for bacterial transformation and a lysate obtained containing the proteinase variants. Release from the cytosol causes the proteinase variant to digest its own propeptide to form the mature protein. The purified proteinase variants can then be assayed for activity as described in Example 1.

Wild type Proteinase K is commonly used for destroying enzymes and their activities in a reaction vessel after the enzymes have completed their functions. When this has been accomplished, the task then becomes how to remove the Proteinase K to permit down-stream enzyme reactions to occur. With a thermolabile proteinase variant such as a Proteinase K variant, raising the temperature to a suitable level selected from the range of 50° C.-70° C. for 5-40 minutes can cause the proteinase activity to be significantly reduced or lost. This removes the need for a purification step of the substrate of interest which invariably results in substrate loss. The proteinase variant may be used in a stream-lined workflow. For example, single cell analysis involves very small amounts of nucleic acids of interest. Thermolabile Proteinase K contributes to a reduction in loss of material of nucleic acids contributing to improved sequence data and improved diagnostics outcomes.

Examples of nucleic acid analyses that benefit from the use of thermolabile Proteinase K include error correction, DNA repair and DNA methylation analyses. These methods and other forms of analyses that utilize multiple enzyme steps benefit from replacing intermediate purification steps involving for example, beads, by the use of thermolabile proteinase.

Molecular biology workflows that benefit from the use of thermolabile Proteinase K include in vitro transcription and in vitro transcription-translation methods that involve large numbers of samples and many proteins. Other workflows include material obtained from cell lysis (including liquid and tissue biopsy material for diagnostics) and amplification workflows.

Workflows for therapeutic nucleic acid production (RNA or DNA) have stringent purity requirements in which case, removal of the products of thermolabile Proteinase K and the inactivated enzyme itself may be desirable in which case a final step may be necessary in which nucleic acids are immobilized and all byproducts of proteinase digestion including inactivated proteinases are removed. Other processes do not require removal of inactivated thermolabile proteinase or amino acid products after digestion of proteins.

Examples of the use of thermolabile proteinase are provided in, for example, Examples 3-5. These include enhancement of yield, and avoidance of adaptor dimer formation after DNA repair of FFPE DNA samples; the reduced loss of RNA after poly-A tailing; and enhanced yield and reduced GC bias in libraries prepared for Illumina sequencing of genomic samples. Proteinase variants may inactivate any one or more of polymerases, ligases, endonucleases, deaminases, kinases, fragmentases, DNA repair enzymes, poly(A) polymerase, end-repair enzymes in a reaction vessel.

The one or more enzymes in the reaction mixture used before, with or after the thermolabile proteinase variant may include one or more enzymes for adding a 3' A-tail to a DNA substrate; ligases for ligating adapters to the DNA, enzymes for A-tailing the DNA for ligating adaptors prior to DNA sequencing, enzymes for reducing dimerization of the adaptors compared with separating enzymes using beads. Purified thermolabile proteinase variants can be used in various molecular biology workflows involving nucleic acid manipulation in a multi-step enzymatic process. For example, thermolabile proteinase variants may be used in a workflow suitable for generating DNA libraries, for example, genomic libraries (see for example New England Biolabs, Ipswich, Mass.) including preparing a sample for sequencing (see for example NEBNext (New England Biolabs, Ipswich, Mass.)), gene assembly or DNA synthesis such as Golden gate assembly, Gibson assembly and NEBuilder® assembly (New England Biolabs, Ipswich, Mass.).

The removal of an intermediate purification step, often using beads, additionally opens up the possibility of automation of multi-step reactions using proteinase variants. Automated workflow platforms include microfluidic devices, for example capillary channels and electronic gates (LabChip® microfluidic platform: Perkin Elmer, Waltham, Mass.) or droplets that move and merge in response to a modulated electrical charge (Umapathi, et al., (2018) MRS Advances, 3 (26), 1475-1483. doi:10.1557/adv.2018.331). In these platforms, enzyme reactions may be performed with greater ease than bead separation steps. The advantages extend to reactions performed in a single tube, well, or other reaction vessel.

An advantage of the present methods using thermolabile proteinase variants in molecular biology workflows is that the substrate nucleic acid sample quantity and quality is effectively preserved by using a mild heat treatment step(s) and avoiding or minimizing the number of bead or column-mediated enzyme removal steps. Mild heating at 55° C., 60° C. or 65° C. to inactivate the thermolabile proteinase activity is minimally detrimental to the nucleic acid substrate thus enabling further enzyme manipulations in a workflow.

Any of the above proteinase variants or compositions thereof may be contained in a kit with instructions for use.

As will be understood by those skilled in the art who have the benefit of this disclosure, other equivalent or alternative proteinase variants compositions, methods of use, and kits can be envisioned without departing from the description contained herein. Persons skilled in the art may make various changes in the kind, number, and/or arrangement of amino acid substitutions in proteinase variants without departing from the spirit or scope of this disclosure. These equivalents and alternatives along with changes and modifications are intended to be included within the scope of the present disclosure. Each disclosed method and method step may be performed in association with any other disclosed method or method step and in any order according to some embodiments. Accordingly, the foregoing disclosure including the disclosed embodiments and examples of variants, compositions, methods, systems, and kits is intended and is to be construed as illustrative only.

Numeric ranges are inclusive of the numbers defining the range. Where the endpoints are approximate, the degree of flexibility may vary in proportion to the order of magnitude of the range. For example, a range endpoint of about 50 in the context of a range of about 5 to about 50 may include 52.5 or 55.

Unless otherwise defined, all technical and scientific terms used herein have the same meaning as commonly understood by one of ordinary skill in the art to which this disclosure belongs. Still, certain elements may be defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

All patents and publications, including all sequences disclosed within such patents and publications, referred to herein including U.S. application Ser. No. 16/718,880, filed Dec. 18, 2019, U.S. Provisional Application No. 62/782,436, filed Dec. 20, 2018, and U.S. Provisional Application No. 62/782,716, filed Dec. 20, 2018, are expressly incorporated by reference.

EXAMPLES

Aspects of the present disclosure can be further understood in light of the following example, which should not be construed as limiting the scope of the present disclosure in any way.

Example 1: Proteinase K Variants can be Heat Inactivated at 55° C.

An assay was developed to evaluate thermostability of Proteinase K variants relative to wild type Proteinase K. Proteinase variants and wild type Proteinase K were expressed in *E. coli* and cell lysates containing the expressed protein are first incubated at various temperatures (e.g., 4° C., 50° C., 55° C., 60° C., or 65° C.). The peptide-based activity assay is then performed at 37° C. to determine the effect of the heat treatment. All variants tested displayed a greater susceptibility to heat treatment (FIG. 3B-FIG. 3F) when compared to wild type Proteinase K (FIG. 3A).

A peptide (N-Succinyl-Ala-Ala-Pro-Phe-pNA, Sigma, S7388) (SEQ ID NO:32) was used as a substrate to monitor the Proteinase K (pK) activity. This four-amino acid peptide is linked to para-nitroanilide (pNA) via a peptide bond between the carboxyl group of phenylalanine and the amine group of pNA. Cleavage of this colorless substrate by Proteinase K liberated yellow pNA. The released pNA absorbed light at 410 nm. Spectrophotometric readings of the yellow pNA product over time provided a measure of Proteinase K activity.

Wild type Proteinase K and five Proteinase K variants were expressed in *E. coli* and the cells lysed. The cell lysates were then subjected to different temperatures (65° C., 60° C., 55° C., and 50° C.) for 15 minutes using a thermocycler machine or not heated (4° C., as a control). The cell lysates (10 uL) were then incubated with 100 μl of reaction mixture containing 1 mM N-Suc-Ala-Ala-Pro-Phe-pNA, 0.1% SDS, 0.1% Triton x-100, 20 mM Tris-HCl pH 8.0, 5 mM $CaCl_2$, and 50 mM NaCl. The reaction mixture containing the mutated Proteinase K or wild type Proteinase K was then incubated at 37° C. to measure proteolysis and to determine residual Proteinase K activity in a Spectramax® M5 (Molecular Devices, Sunnyvale, Calif.) plate reader. Absorbance at 410 nm was measured every 30 seconds. The Proteinase K activity is visualized by the initial linear curve or calculated by the initial linear rate. Importantly, wild type Proteinase K retained near full activity after heat treatments using 65° C., 60° C., 55° C., and 50° C. (FIG. 3A).

Proteinase K variants including the Y236H substitution in the alpha helix region of SEQ ID NO:12 were found to be more thermolabile (FIG. 3D-FIG. 3F) than the equivalent proteins with tyrosine retained at position 236 (FIG. 3A-FIG. 3C). Variants that did not include a substitution within the alpha helix region showed enzyme activity after heat treatment at 55° C. that was similar to wild type Proteinase K and showed some activity after heat treatment at 60° C.

Heat-treated *E. coli* cell lysates were also assayed for activity by incubation with protein substrate bovine serum albumin (BSA). FIG. 4 shows that the Proteinase K variant named 16YH containing substitutions (Y236H, V77I, R147N, G203A, K242R and P265S) was not capable of digesting BSA after a 60° C. heat treatment (lane 4). In contrast, recombinant wild type Proteinase K (Sigma-Aldrich, St. Louis, Mo.) retained full activity on BSA after heat treatments using 60° C., 65° C., 70° C. and 75° C. Likewise, native wild type Proteinase K (New England Biolabs, Ipswich, Mass.) retained activity on BSA after heat treatments using temperatures of 60° C., 65° C., 70° C. and 75° C. (FIG. 4).

Example 2: Enhanced Thermolability of Proteinase K Variants with Substitutions within Helix 3

Example 1 and FIG. 3A-FIG. 4 describe Proteinase K variants where the thermostability is reduced and therefore thermolability is increased relative to wild type Proteinase K. The Y236H variant (FIG. 3D) displays a significant reduction of thermostability relative to wild type Proteinase K (FIG. 3A) and two other variants including the Y236H substitution (FIG. 3E and FIG. 3F) display a significant reduction of thermostability relative to variants without the Y236H substitution (FIG. 3B and FIG. 3C). In light of these results, 18 other amino acid substitutions (other than Y236H) were made at position 236. Additionally, other residues in the same hydrophobic alpha-helix (helix 3, amino acids 230-237) were mutated to determine the respective effect on Proteinase K thermostability. Amino acids substitutions V230T and L233N were also generated and the resulting single amino acid variants were assayed for thermostability.

The assay described in Example 1 was employed to analyze the substitutions made within the hydrophobic alpha helix (corresponding to SEQ ID NO:12). The variants were expressed in *E.coli* and cell lysates were prepared. The cell lysates containing the expressed variants were first incubated at various temperatures: 4° C., 50° C., 55° C., 60° C. and 65° C. for 15 minutes. The peptide-based activity assay was then performed at 37° C. to determine the effect of the heat treatment on Proteinase K activity.

In other experiments, thermolabile Proteinase K activity was tested 4° C., 10° C., 20° C., and 37° C. and 42° C. and was found to be active. Incubation was performed at these time points for 1 hour and overnight when BSA was used as a substrate.

Variations occurred among the mutants as to what temperature achieved substantially complete reduction in activity in a 5-minute, 10 minute or 15-minute incubation. For some variants, 50° C. was sufficient (Proteinase K Y236K and Y236R mutants are killed after 50° C. for 15 minutes (FIG. 8B). However, for example Proteinase K (Y2361) was still quite active after treatment at 50° C. for 15 minutes but was substantially inactive at 60° C. and appeared completely inactive at 65° C.

All variants tested displayed a greater susceptibility to heat treatment (FIG. 8B-FIG. 8F) when compared to wild type Proteinase K. The data in FIG. 8B-FIG. 8F is displayed with Activity (%) on the y-axis. This activity level is the rate of product formation over time (Vmax, slope of the curve during the linear phase) as measured by a Spectramax® M5 (Molecular Devices, Sunnyvale, Calif.) plate reader. Absorbance at 410 nm was measured every 30 seconds for a total of 40 minutes. For each individual variant, the activity remaining after heat treatment (incubation at 50° C., 55° C., 60° C. or 65° C.) is plotted relative to the activity without heat treatment (incubation at 4° C. for 15 minutes). In each plot, the activity of wild type Proteinase K treated at 4° C. is set at 100% and importantly all heat treatments (50° C., 55° C., 60° C. and 65° C.) did not reduce the activity of wild type Proteinase K. In contrast, all variants tested in FIG. 8B-FIG. 8F displayed a reduction of activity at 50° C. and/or 55° C. and/or 60° C. and/or 65° C. relative to 4° C.

Example 3: Thermolabile Proteinase K Variant Improves Enzymatic DNA Repair Within Formalin-Fixed Paraffin-Embedded (FFPE) Samples A workflow was designed and implemented to utilize a thermolabile Proteinase K (TL-Proteinase K) to remove DNA repair enzymes from FFPE repaired DNA samples in a workflow for sequencing on an Illumina platform. All reagents and kits used were obtained commercially from New England Biolabs, Ipswich, Mass.

The first step of the workflow used a multi-enzyme cocktail of DNA Repair enzymes for repairing damage such as nicks, gaps, and abasic sites, cytosine deamination, oxidative damage, and UV damage. After repair of the DNA, a separation step was introduced into the workflow prior to Ultra II DNA library preparation including End Prep (end repair and A-tailing) and adaptor ligation to prevent adaptor ligation that otherwise was found to occur.

The introduction of a bead separation step resulted in no detectable adapter dimerization but there was a significant loss of material. However, when a thermolabile Proteinase K described in Example 1 (for example, 2YH or 16YH) having a modification at position 236 was used at 37° C. to degrade the repair enzymes followed by an inactivation step at 60° C., not only were no adaptor dimers detected but there was significantly less loss of DNA than otherwise occurred using beads. These improvements were particularly significant because of the generally low amounts of input DNA and the poor sample quality.

Figures 5A, 5B, 5C:
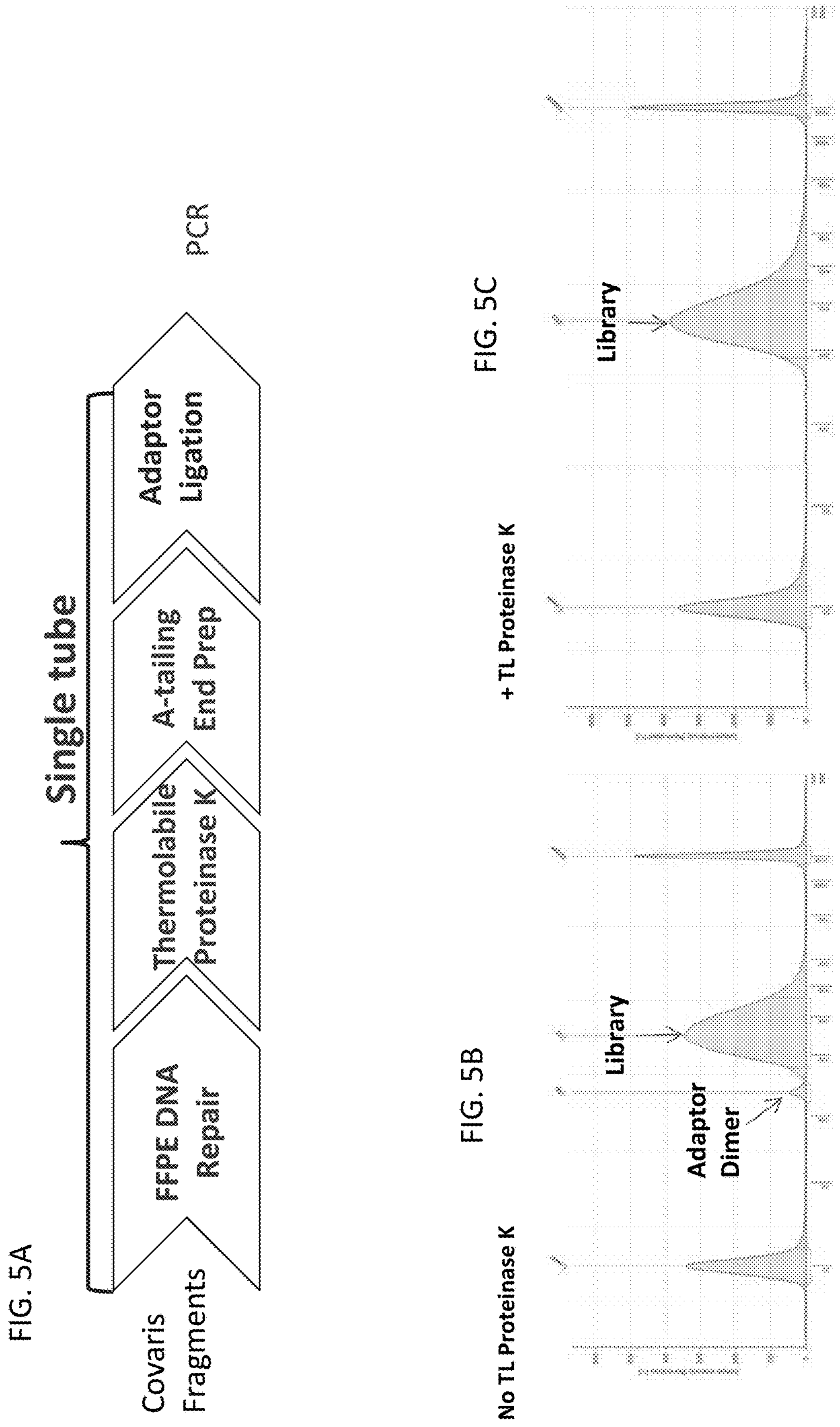
FIG. 5A-FIG. 5C illustrates the use of a thermolabile proteinase to remove repair enzymes prior to preparation of a DNA sequencing library. The Proteinase K variant was either 2YH or 16YH in FIGS. 3E and 3F.

The workflow shown in FIG. 5A utilized a repair mix of enzymes (NEBNext FFPE DNA Repair, New England Biolabs, Ipswich, Mass.) followed by incubation with the thermolabile Proteinase K as described in Example 1 followed by end repair and A-tailing (Ultra II, New England Biolabs, Ipswich, Mass.) and adapter ligation (New England Biolabs, Ipswich, Mass.) followed by PCR. The amplified DNA was sequenced on an Illumina sequencing machine.

Libraries prepared with FFPE DNA Repair library prep kit were loaded on the TapeStation® 4200 (Agilent, Santa Clara, Calif.) to assess library size, yield, and purity. FIG. 5B indicate a library (arrow) prepared with NEBNext FFPE DNA Repair where repair enzymes remained in solution through End Prep and Adaptor Ligation and adaptor dimer is observed (arrow). Libraries treated with thermolabile Proteinase K after treatment with NEBNext FFPE DNA Repair showed no detectable adaptor dimer.

Example 4: Optimizing Nanopore Direct Sequencing of Bacterial RNA with Thermolabile Proteinase K Variant for Enzyme Inactivation Nanopore sequencing technology enables real-time strand-specific RNA sequencing for directly detecting nucleotide modifications or analogs and avoids reverse transcription or amplification bias. However, practical deployment of the technology can be hampered by the requirement of relatively high input of the RNA from a biological sample. Given insufficient sample, this limitation can significantly affect coverage depth, accuracy of the sequence reads and sensitivity in microbial detection.

An improved workflow utilizing a thermolabile Proteinase K such as 2YH or 16YH described in FIG. 3E and FIG. 3F to substitute for a bead-based purification step, resulted in improved RNA recovery yield. This new approach enables generation of significantly more reads from direct sequencing of bacterial RNA on Nanopore MinION® (Oxford Nanopore Technologies, Oxford, UK) and is suitable for sequencing of lower abundance RNA sample. A major source of RNA loss during the multi-step sample preparation results from bead-based purification steps. Traditional RNA sample preparation protocols include a two-step, cascade ligation of adaptors, with each step followed by the use of RNA-binding beads to remove the unligated adaptor.

The use of a thermolabile Proteinase K to inactivate poly(A) polymerase can circumvent the requirement for physically removing the enzyme by use of beads, resulting in an increase in total reads from sequencing on Nanopore MinION.

Figure 6A:
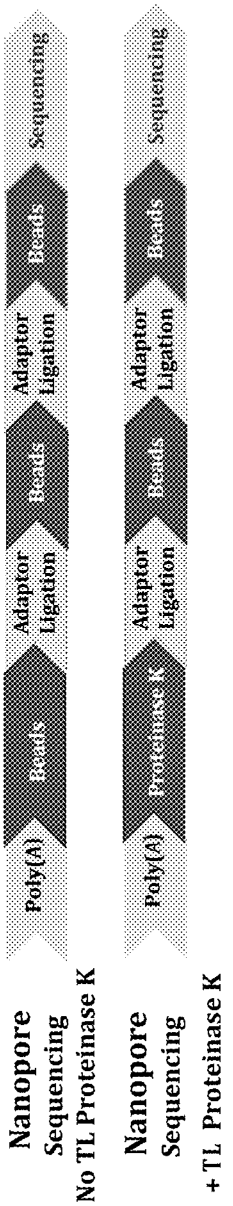
FIG. 6A-FIG. 6B illustrates a workflow that uses a thermolabile proteinase for sample preparation for Oxford Nanopore sequencing of RNA. Use of a thermolabile Proteinase K in this method results in an improved yield. The Proteinase K variant was either 2YH or 16YH in FIG. 3E and FIG. 3F.
Figure 6B:
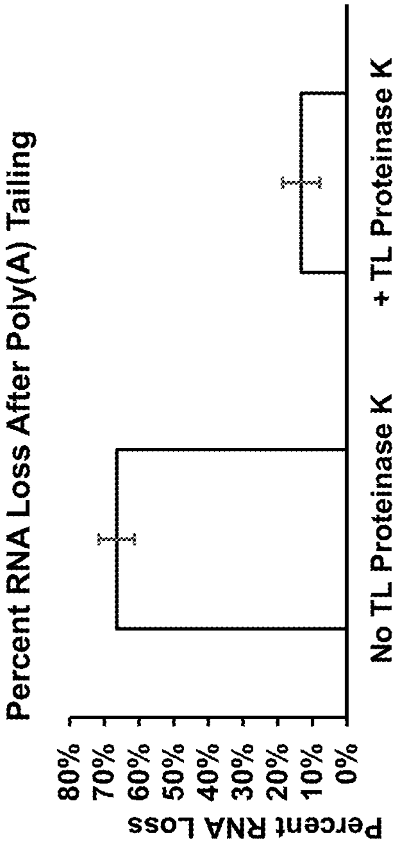

1000 ng of *E. coli* RNA was incubated in 20 μl with 2 units of *E. coli* Poly(A) Polymerase (New England Biolabs, Ipswich, Mass.) in the presence of 1× Poly(A) Polymerase Buffer, 1 mM ATP at 37° C. for 30 minutes. A 10-fold dilution of Thermolabile Proteinase K (described in FIG. 3D or FIG. 3F) was prepared by diluting 1 μl of an enzyme stock (1.25 mg/mL) into 9 μl of 1× Poly(A) Polymerase Buffer. 1 μl of the diluted Proteinase K was added to the polyadenylated RNA sample followed by incubation at 20° C. for 15 minutes and then at 55° C. for 15 minutes. For the control sample, the polyadenylated RNA sample was purified by beads according to the original protocol of Nanopore. 1 μl from each RNA sample was measured using Qubit® (ThermoFisher Scientific, Waltham, Mass.) to determine the RNA concentrations and recovery percentages following thermolabile Proteinase K treatment or bead purification (FIG. 6B).

For sequencing on a Nanopore MinION, 300 ng of input *E. coli* RNA was polyadenylated, processed by either thermolabile Proteinase K or bead purification and then subjected to ligation with for real time analysis (RTA). The poly(A) tailed RNA samples were processed by the thermolabile Proteinase K procedure or bead purification as described above. Next, each sample was ligated to 100 nM pre-annealed splint adapter RTA using T4 DNA ligase. The products were purified using a 1.8 μl of Agencourt AMPure® beads (Beckman Coulter, Brea, Calif.) per μl of sample, washing twice in 70% ethanol. Sequencing adapters (RMX) preloaded with motor protein were then ligated onto the RNA:adaptor hybrid duplex. The final library was cleaned up using 1.8 μl of AMPure beads per μl of sample. The library was then mixed with running buffer to 150 μl and injected into an R9 flow cell and run on a Mk1b MinION. As shown in FIG. 6B, the protocol with thermolabile Proteinase K exhibits significantly higher sequencing reads from the 300 ng input *E. coli* RNA compared to the Nanopore protocol.

Example 5: Use of Thermolabile Proteinase K Variant Enables Library Construction for Next-Generation Sequencing on Illumina Platform The use of thermolabile Proteinase K for effectively degrading enzymes used in a DNA end repair step during library construction and then being degraded in turn by heat treatment at 55° C. was tested. This next generation workflow was demonstrated to enable high quality library products with improved sequence coverage metrics when compared to standard workflows.

Figure 7A:
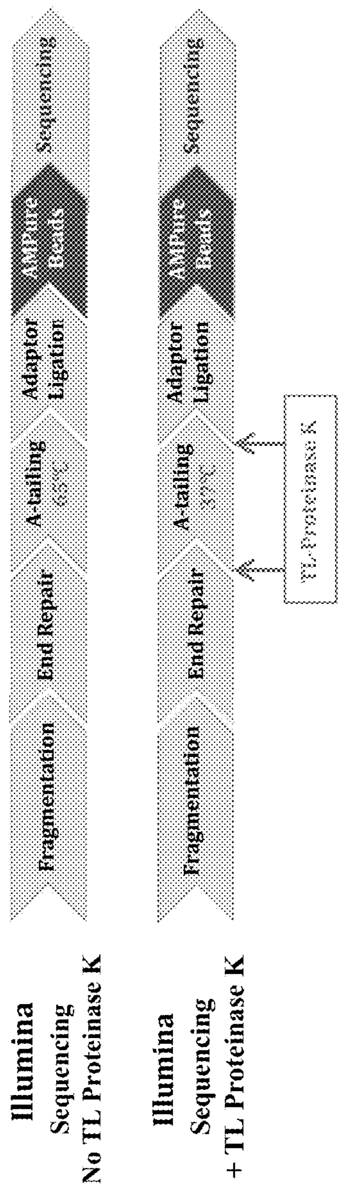
FIG. 7A-FIG. 7C shows that the use of thermolabile Proteinase K can reduce sample loss after A-tailing of sample DNA, thereby increasing the yield of amplified genomic DNA fragments that are ligated to adaptors for sequencing and improving sequence coverage by reducing GC bias. The Proteinase K variant was either 2YH or 16YH in FIG. 3E and FIG. 3F.

A standard protocol of amplification-free library preparation for the Illumina NGS platform comprises fragmentation, end repair (blunting and 5' phosphorylation), 3' A-tailing and adaptor ligation (FIG. 7A). Once the sample DNA had been randomly sheared, the fragment ends were repaired by blunting and 5' phosphorylation with a mixture of enzymes, such as T4 polynucleotide kinase and T4 DNA polymerase. This end repair step was followed by 3' A-tailing at elevated temperatures using a thermophilic polymerase such as Taq DNA polymerase. Alternatively, bead-based purification could be used to physically remove the end repair enzymes prior to A-tailing at 37° C. with a mesophilic polymerase such as Klenow Fragment 3'-5' exonuclease minus. Bead purification, however, was known to cause sample loss whereas high temperature incubation appeared to be a key contributory factor responsible for generating sequence coverage bias (Zhang et al., Scientific Reports, 8: 415887, 2018).

In this example, end repair enzymes were inactivated using thermolabile Proteinase K (FIG. 3E or FIG. 3F); thereby eliminating a bead purification step. The Proteinase K was then inactivated by raising the temperature to 55° C., without disrupting the nucleic acid substrate. The thermolabile Proteinase K modified workflow enabled production of high yield human DNA libraries with a reduced sequence coverage bias for sequencing a human genome on an Illumina MiSeq® (Illumina, San Diego, Calif.).

Figure 7B:
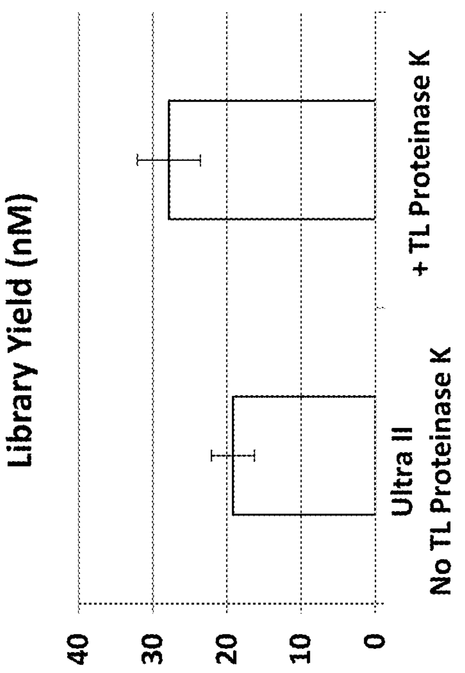

Human genomic DNA (Mix), obtained from Promega (Fitchburg, Wis.), was diluted to a final concentration of 100 μg/ml in 10 mM Tris-HCl, 1 mM EDTA, pH 7.5, and fragmented to 200 base pairs (bp) using a Covaris AFA S2 system (Covaris, Woburn, Mass.). Each PCR-free library was made using 1 μg of fragmented genomic DNA. Duplicate control libraries were prepared according to the protocol of NEBNext Ultra II Library Prep Kit (Ultra II) where end repair was achieved at 20° C. for 30 minutes followed by incubation at 65° C. for 30 minutes for 3' A-tailing. Duplicate libraries were also prepared according to the Ultra II protocol substituting thermolabile Proteinase K for a bead purification step. For the protocol modified with Proteinase K treatment, 1 μL of 0.05 mg/mL of TL-Proteinase K (freshly diluted by 10 folds from a 0.5 mg/ml stock) was added to each end repair reaction, followed by incubation at 20° C. for 15 minutes and 55° C. for 15 minutes. The reaction was then incubated at 37° C. for 30 minutes after addition of 3 μl of Taq DNA polymerase (5,000 units/mL). For both protocols, each library was ligated to pre-annealed full-length paired-end Illumina adaptors (Illumina TruSeq® DNA PCR-free Library Prep Kit (Illumina, San Diego, Calif.)). All DNA libraries were size-selected and analyzed to determine the size distribution using an Agilent High Sensitivity DNA Kit on a Bioanalyzer 2100 (Agilent Technologies, Santa Clara, Calif.). Library yields were further determined by qPCR using the NEBNext library quant kit for Illumina. As shown in FIG. 7A-FIG. 7B, the TL-Proteinase K protocol generated high yield DNA libraries compared to the Ultra II control libraries.

Figure 7C:
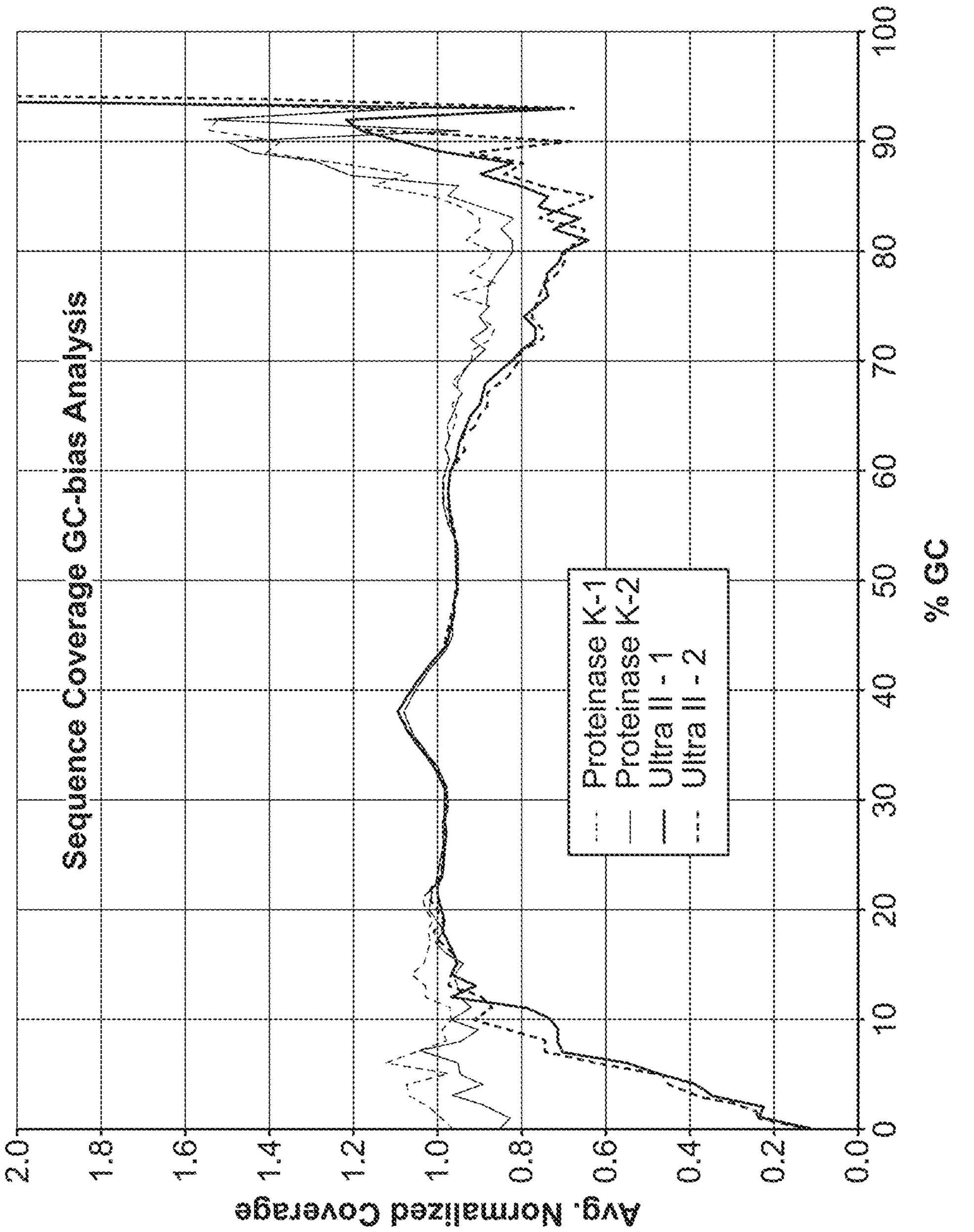

The amplification-free indexed libraries were mixed and sequenced on an Illumina MiSeq in paired-end mode (2×75 bp). Reads were adapter trimmed before alignment to the reference genome. GC bias was assessed using Picard's CollectGCBiasMetrics (Picard 2.7.1). Relevant Low-GC regions were identified by intersecting 100 bp windows (bedtools v2.25.0) having GC fraction <0.2 with 80% overlap with features in the GENCODE v26 basic genes. Coverage of low GC regions was assessed using bedtools v2.25.0. As shown in FIG. 7C, use of this TL-Proteinase K protocol resulted in significantly lower GC-bias with higher sequence coverage of high AT-content regions of human DNA libraries compared to the workflow using beads. In addition, the major metrics of Illumina sequencing quality from the libraries prepared by either using thermolabile Proteinase K inactivated by a raised temperature (65° C.) or wild type Proteinase K using beads were similar. Thus, TL-Proteinase K can be used to effectively inactivate enzymes after the end repair step, and to allow for high quality library construction.

It will be recognized by those skilled in the art that, while the disclosure has been described above in terms of preferred embodiments, it is not limited thereto. Various features and aspects may be used individually or jointly. Further, although described in the context of its implementation in a particular environment, and for particular applications, those skilled in the art will recognize that the usefulness of disclosed variants, compositions, methods, kits, and other embodiments is not limited thereto and that the embodiments and examples of the present disclosure can be beneficially utilized in any number of environments and implementations. Accordingly, the claims set forth below should be construed in view of the full breadth and spirit of this disclosure. All references cited herein are incorporated by reference.

What is claimed is:

1. A method for degrading protein, comprising:

incubating a sample comprising the protein with a thermolabile protease at a temperature that is below 50° C., wherein i. the thermolabile protease has an amino acid sequence is at least 90% identical to SEQ ID NO: 1 and ii. the amino acid at the position corresponding to position 236 in SEQ ID NO: 1 in the protease is an amino acid other than tyrosine but not proline.

2. The method of claim 1, wherein the protein is an enzyme.

3. The method of claim 1, wherein the sample further comprises nucleic acid.

4. The method of claim 1, further comprising:

raising the temperature to at least 60° C. for a period of time to inactivate the thermolabile protease.

5. The method of claim 2, wherein the period of time is in the range of 5 minutes-40 minutes.

6. The method of claim 4, further comprising adding an additional enzyme to the sample after the thermolabile protease is inactivated.

7. The method of claim 1, wherein the amino acid at the position corresponding to position 236 in SEQ ID NO: 1 in the protease is a histidine (H).

8. The method of claim 1, wherein the thermolabile protease comprises one or more substitutions at one or more positions corresponding to positions V77, R147, G203, K242, S247 and P265 in SEQ ID NO:1.

* * * * *

SEQUENCE LISTING

```
<160> NUMBER OF SEQ ID NOS: 32

<210> SEQ ID NO 1
<211> LENGTH: 279
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: GenBank P06873.2 mature form of Proteinase K

<400> SEQUENCE: 1

Ala Ala Gln Thr Asn Ala Pro Trp Gly Leu Ala Arg Ile Ser Ser Thr
1               5                   10                  15

Ser Pro Gly Thr Ser Thr Tyr Tyr Tyr Asp Glu Ser Ala Gly Gln Gly
            20                  25                  30

Ser Cys Val Tyr Val Ile Asp Thr Gly Ile Glu Ala Ser His Pro Glu
        35                  40                  45

Phe Glu Gly Arg Ala Gln Met Val Lys Thr Tyr Tyr Tyr Ser Ser Arg
    50                  55                  60

Asp Gly Asn Gly His Gly Thr His Cys Ala Gly Thr Val Gly Ser Arg
65                  70                  75                  80

Thr Tyr Gly Val Ala Lys Lys Thr Gln Leu Phe Gly Val Lys Val Leu
                85                  90                  95

Asp Asp Asn Gly Ser Gly Gln Tyr Ser Thr Ile Ile Ala Gly Met Asp
            100                 105                 110
```

-continued

```
Phe Val Ala Ser Asp Lys Asn Asn Arg Asn Cys Pro Lys Gly Val Val
        115                 120                 125

Ala Ser Leu Ser Leu Gly Gly Gly Tyr Ser Ser Ser Val Asn Ser Ala
    130                 135                 140

Ala Ala Arg Leu Gln Ser Ser Gly Val Met Val Ala Val Ala Ala Gly
145                 150                 155                 160

Asn Asn Asn Ala Asp Ala Arg Asn Tyr Ser Pro Ala Ser Glu Pro Ser
                165                 170                 175

Val Cys Thr Val Gly Ala Ser Asp Arg Tyr Asp Arg Arg Ser Ser Phe
            180                 185                 190

Ser Asn Tyr Gly Ser Val Leu Asp Ile Phe Gly Pro Gly Thr Ser Ile
        195                 200                 205

Leu Ser Thr Trp Ile Gly Gly Ser Thr Arg Ser Ile Ser Gly Thr Ser
    210                 215                 220

Met Ala Thr Pro His Val Ala Gly Leu Ala Ala Tyr Leu Met Thr Leu
225                 230                 235                 240

Gly Lys Thr Thr Ala Ala Ser Ala Cys Arg Tyr Ile Ala Asp Thr Ala
                245                 250                 255

Asn Lys Gly Asp Leu Ser Asn Ile Pro Phe Gly Thr Val Asn Leu Leu
            260                 265                 270

Ala Tyr Asn Asn Tyr Gln Ala
        275


<210> SEQ ID NO 2
<211> LENGTH: 278
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: mature form of Genbank Accession No. P23653.1

<400> SEQUENCE: 2

Ala Glu Gln Arg Asn Ala Pro Trp Gly Leu Ala Arg Ile Ser Ser Thr
1               5                   10                  15

Ser Pro Gly Thr Ser Thr Tyr Arg Tyr Asp Asp Ser Ala Gly Gln Gly
            20                  25                  30

Thr Cys Val Tyr Val Ile Asp Thr Gly Val Glu Ala Ser His Pro Glu
        35                  40                  45

Phe Glu Gly Arg Ala Gln Met Val Lys Thr Tyr Tyr Ala Ser Ser Arg
    50                  55                  60

Asp Gly Asn Gly His Gly Thr His Cys Ala Gly Thr Ile Gly Ser Arg
65                  70                  75                  80

Thr Tyr Gly Val Ala Lys Lys Thr Gln Ile Phe Gly Val Lys Val Leu
                85                  90                  95

Asn Asp Gln Gly Ser Gly Gln Tyr Ser Thr Ile Ile Ser Gly Met Asp
            100                 105                 110

Phe Val Ala Asn Asp Tyr Arg Asn Arg Asn Cys Pro Asn Gly Val Val
        115                 120                 125

Ala Ser Met Ser Ile Gly Gly Gly Tyr Ser Ser Ser Val Asn Ser Ala
    130                 135                 140

Ala Ala Asn Leu Gln Gln Ser Gly Val Met Val Ala Val Ala Ala Gly
145                 150                 155                 160

Asn Asn Asn Ala Asp Ala Arg Asn Tyr Ser Pro Ala Ser Glu Ser Ser
                165                 170                 175
```

```
Ile Cys Thr Val Gly Ala Thr Asp Arg Tyr Asp Arg Arg Ser Ser Phe
            180                 185                 190

Ser Asn Tyr Gly Ser Val Leu Asp Ile Phe Ala Pro Gly Thr Asp Ile
        195                 200                 205

Leu Ser Thr Trp Ile Gly Gly Ser Thr Arg Ser Ile Ser Gly Thr Ser
    210                 215                 220

Met Ala Thr Pro His Val Ala Gly Leu Ala Ala Tyr Leu Met Thr Leu
225                 230                 235                 240

Gly Arg Ala Thr Ala Ser Asn Ala Cys Arg Tyr Ile Ala Gln Thr Ala
                245                 250                 255

Asn Gln Gly Asp Leu Ser Asn Ile Ser Phe Gly Thr Val Asn Leu Leu
            260                 265                 270

Ala Tyr Asn Asn Tyr Gln
        275


<210> SEQ ID NO 3
<211> LENGTH: 278
<212> TYPE: PRT
<213> ORGANISM: Artificial Sequence
<220> FEATURE:
<223> OTHER INFORMATION: Synthetic construct

<400> SEQUENCE: 3

Ala Glu Gln Arg Asn Ala Pro Trp Gly Leu Ala Arg Ile Ser Ser Thr
1               5                   10                  15

Ser Pro Gly Thr Ser Ser Tyr Arg Tyr Asp Glu Ser Ala Gly Gln Gly
            20                  25                  30

Thr Cys Val Cys Val Ile Asp Thr Gly Val Glu Ala Ser His Pro Glu
        35                  40                  45

Phe Glu Gly Arg Ala Gln Met Val Lys Thr Tyr Tyr Ser Ser Ser Arg
    50                  55                  60

Asp Gly Asn Gly His Gly Thr His Cys Ala Gly Thr Ile Gly Ser Arg
65                  70                  75                  80

Thr Tyr Gly Val Ala Lys Lys Thr Gln Ile Phe Gly Val Lys Val Leu
                85                  90                  95

Asn Asp Gln Gly Ser Ser Gln Tyr Ser Thr Ile Ile Ser Gly Met Asp
            100                 105                 110

Phe Val Ala Asn Asp Tyr Arg Asn Arg Asn Cys Pro Asn Gly Val Val
        115                 120                 125

Ala Ser Met Ser Ile Gly Gly Gly Tyr Ser Ser Ser Val Asn Ser Ala
    130                 135                 140

Ala Ala Asn Leu Gln Gln Ser Gly Val Met Val Ala Val Ala Ala Gly
145                 150                 155                 160

Asn Asn Asn Ala Asp Ala Arg Asn Tyr Ser Pro Ala Ser Glu Ser Ser
                165                 170                 175

Ile Cys Thr Val Gly Ala Thr Asp Arg Tyr Asp Arg Arg Ser Ser Phe
            180                 185                 190

Ser Asn Tyr Gly Ser Val Leu Asp Ile Phe Ala Pro Gly Thr Asp Ile
        195                 200                 205

Ile Ser Thr Trp Ile Gly Gly Thr Thr Arg Ile Ile Ser Gly Thr Ser
    210                 215                 220

Met Ala Thr Pro His Val Ala Gly Leu Ala Ala Tyr Phe Met Thr Leu
225                 230                 235                 240

Gly Arg Ala Thr Ala Ser Asn Ala Cys Arg Tyr Ile Ala Gln Thr Ala
                245                 250                 255
```

```
Asn Gln Gly Asp Leu Ser Gly Ile Pro Phe Gly Thr Val Asn Leu Leu
            260                 265                 270

Ala Tyr Asn Asn Tyr Gln
        275


<210> SEQ ID NO 4
<211> LENGTH: 274
<212> TYPE: PRT
<213> ORGANISM: Artificial Sequence
<220> FEATURE:
<223> OTHER INFORMATION: Synthetic construct

<400> SEQUENCE: 4

Thr Thr Gln Thr Gly Ala Pro Trp Gly Leu Gly Arg Ile Ser His Arg
1               5                   10                  15

Ala Lys Gly Ser Thr Ser Tyr Thr Tyr Asp Thr Ser Ala Gly Glu Gly
            20                  25                  30

Thr Cys Val Tyr Val Ile Asp Thr Gly Val Glu Asp Thr His Pro Glu
        35                  40                  45

Phe Glu Gly Arg Ala Lys Leu Ile Lys Thr Tyr Tyr Gly Asn Arg Asp
    50                  55                  60

Gly His Gly His Gly Thr His Cys Ser Gly Thr Ile Gly Ser Lys Thr
65                  70                  75                  80

Tyr Gly Val Ala Lys Lys Thr Lys Ile Tyr Gly Val Lys Val Leu Asp
                85                  90                  95

Asp Asn Gly Ser Gly Thr Phe Ser Asn Ile Ile Ala Gly Val Asp Phe
            100                 105                 110

Val Ala Asn Asp Tyr Lys Thr Arg Gly Cys Pro Lys Gly Ala Val Ala
        115                 120                 125

Ser Met Ser Leu Gly Gly Gly Lys Thr Gln Ala Val Asn Asp Ala Val
    130                 135                 140

Ala Arg Leu Gln Arg Ala Gly Val Phe Val Ala Val Ala Ala Gly Asn
145                 150                 155                 160

Asp Asn Thr Asp Ala Ala Asn Thr Ser Pro Ala Ser Glu Pro Ser Val
                165                 170                 175

Cys Thr Val Gly Ala Ser Asp Lys Asp Asp Val Arg Ser Thr Phe Ser
            180                 185                 190

Asn Tyr Gly Ser Val Val Asp Ile Phe Ala Pro Gly Thr Ala Ile Leu
        195                 200                 205

Ser Thr Trp Ile Gly Gly Arg Thr Asn Thr Ile Ser Gly Thr Ser Met
    210                 215                 220

Ala Thr Pro His Ile Ala Gly Leu Ala Ala Tyr Leu Met Gly Lys Asp
225                 230                 235                 240

Gly Ala Val Ala Ala Gly Leu Cys Ala Lys Ile Ala Gln Thr Ala Thr
                245                 250                 255

Arg Asn Val Leu Arg Asn Ile Pro Ala Gly Thr Ile Asn Ala Leu Ala
            260                 265                 270

Phe Asn


<210> SEQ ID NO 5
<211> LENGTH: 277
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: mature form of Genbank Accession No.
```

-continued xp_014549317.1

<400> SEQUENCE: 5

Thr Glu Gln Ser Gly Ala Pro Trp Gly Leu Gly Arg Ile Ser His Arg
1 5 10 15

Gln Lys Gly Ser Thr Thr Tyr Arg Tyr Asp Asp Ser Ala Gly Glu Gly
20 25 30

Thr Cys Val Tyr Ile Ile Asp Thr Gly Ile Glu Ala Ser His Pro Glu
35 40 45

Phe Glu Gly Arg Ala Thr Phe Leu Lys Ser Phe Ile Ser Gly Gln Thr
50 55 60

Ser Asp Gly His Gly His Gly Thr His Cys Ala Gly Thr Ile Gly Ser
65 70 75 80

Lys Ser Tyr Gly Val Ala Lys Lys Ala Lys Leu Tyr Gly Val Lys Val
85 90 95

Leu Asp Asn Gln Gly Ser Gly Ser Tyr Ser Gly Ile Ile Ser Gly Met
100 105 110

Asp Tyr Val Ala Gln Asp Ser Lys Thr Arg Gly Cys Pro Lys Gly Ala
115 120 125

Ile Ala Ser Met Ser Leu Gly Gly Gly Tyr Ser Ala Ser Val Asn Gln
130 135 140

Gly Ala Ala Ala Leu Val Asn Ser Gly Val Phe Leu Ala Val Ala Ala
145 150 155 160

Gly Asn Asp Asn Arg Asp Ala Gln Asn Thr Ser Pro Ala Ser Glu Pro
165 170 175

Ser Ala Cys Thr Val Gly Ala Thr Asp Ser Asn Asp Asn Arg Ser Ser
180 185 190

Phe Ser Asn Tyr Gly Lys Val Val Asp Ile Phe Ala Pro Gly Thr Gly
195 200 205

Val Leu Ser Thr Trp Ile Gly Gly Ser Thr Asn Thr Ile Ser Gly Thr
210 215 220

Ser Met Ala Thr Pro His Ile Ala Gly Leu Ala Ala Tyr Leu Ser Ala
225 230 235 240

Leu Gln Gly Lys Thr Thr Pro Ala Ala Leu Cys Lys Lys Ile Gln Asp
245 250 255

Thr Ala Thr Lys Asn Ala Leu Lys Gly Val Pro Ser Gly Thr Val Asn
260 265 270

Tyr Leu Ala Tyr Asn
275

<210> SEQ ID NO 6
<211> LENGTH: 277
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: mature form of Genbank Accession No.
XP_00782186.4

<400> SEQUENCE: 6

Thr Glu Gln Ser Gly Ala Pro Trp Gly Leu Gly Arg Ile Ser His Arg
1 5 10 15

Ser Lys Gly Ser Thr Thr Tyr Arg Tyr Asp Asp Ser Ala Gly Gln Gly
20 25 30

Thr Cys Val Tyr Ile Ile Asp Thr Gly Ile Glu Ala Ser His Pro Glu

-continued 35 40 45

Phe Glu Gly Arg Ala Thr Phe Leu Lys Ser Phe Ile Ser Gly Gln Asn
50 55 60

Thr Asp Gly His Gly His Gly Thr His Cys Ala Gly Thr Ile Gly Ser
65 70 75 80

Lys Thr Tyr Gly Val Ala Lys Lys Ala Lys Leu Tyr Gly Val Lys Val
85 90 95

Leu Asp Asn Gln Gly Ser Gly Ser Tyr Ser Gly Ile Ile Ser Gly Met
100 105 110

Asp Tyr Val Ala Gln Asp Ser Lys Thr Arg Gly Cys Pro Asn Gly Ala
115 120 125

Ile Ala Ser Met Ser Leu Gly Gly Gly Tyr Ser Ala Ser Val Asn Gln
130 135 140

Gly Ala Ala Ala Leu Val Asn Ser Gly Val Phe Leu Ala Val Ala Ala
145 150 155 160

Gly Asn Asp Asn Arg Asp Ala Gln Asn Thr Ser Pro Ala Ser Glu Pro
165 170 175

Ser Ala Cys Thr Val Gly Ala Ser Ala Glu Asn Asp Ser Arg Ser Ser
180 185 190

Phe Ser Asn Tyr Gly Arg Val Val Asp Ile Phe Ala Pro Gly Ser Asn
195 200 205

Val Leu Ser Thr Trp Ile Gly Gly Arg Thr Asn Thr Ile Ser Gly Thr
210 215 220

Ser Met Ala Thr Pro His Ile Ala Gly Leu Ala Ala Tyr Leu Ser Ala
225 230 235 240

Leu Gln Gly Lys Thr Thr Pro Ala Ala Leu Cys Lys Lys Ile Gln Asp
245 250 255

Thr Ala Thr Lys Asn Val Leu Thr Gly Val Pro Ser Gly Thr Val Asn
260 265 270

Tyr Leu Ala Tyr Asn
275

<210> SEQ ID NO 7
<211> LENGTH: 281
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: mature form of Genbank Accession No. ACV71832.1

<400> SEQUENCE: 7

Thr Glu Gln Ser Gly Ala Pro Trp Gly Leu Gly Arg Ile Ser His Arg
1 5 10 15

Ser Arg Gly Ser Thr Thr Tyr Arg Tyr Asp Asp Ser Ala Gly Glu Gly
20 25 30

Thr Cys Val Tyr Ile Ile Asp Thr Gly Ile Glu Ala Ser His Pro Glu
35 40 45

Phe Glu Gly Arg Ala Thr Phe Leu Lys Ser Phe Ile Ser Gly Gln Thr
50 55 60

Thr Asp Gly His Gly His Gly Thr His Cys Ala Gly Thr Ile Gly Ser
65 70 75 80

Arg Ser Tyr Gly Val Ala Lys Lys Ala Lys Leu Tyr Gly Val Lys Val
85 90 95

Leu Asp Asn Gln Gly Ser Gly Ser Tyr Ser Gly Ile Ile Ser Gly Met

-continued

```
            100                 105                 110

Asp Tyr Val Ala Gln Asp Ser Lys Thr Arg Gly Cys Pro Lys Gly Ala
        115                 120                 125

Ile Ala Ser Met Ser Leu Gly Gly Gly Tyr Ser Ala Ser Val Asn Gln
    130                 135                 140

Gly Ala Ala Ala Leu Val Asn Ser Gly Val Phe Leu Ala Val Ala Ala
145                 150                 155                 160

Gly Asn Asp Asn Arg Asp Ala Gln Asn Thr Ser Pro Ala Ser Glu Pro
                165                 170                 175

Ser Ala Cys Thr Val Gly Ala Ser Ala Glu Asn Asp Ser Arg Ser Ser
            180                 185                 190

Phe Ser Asn Tyr Gly Lys Val Val Asp Ile Phe Ala Pro Gly Ser Asn
        195                 200                 205

Val Leu Ser Thr Trp Ile Gly Gly Arg Thr Asn Thr Ile Ser Gly Thr
    210                 215                 220

Ser Met Ala Thr Pro His Ile Ala Gly Leu Ala Ala Tyr Leu Ser Ala
225                 230                 235                 240

Leu Gln Gly Lys Thr Thr Pro Ala Ala Leu Cys Lys Lys Ile Gln Asp
                245                 250                 255

Thr Ala Thr Lys Asn Ala Leu Thr Gly Val Pro Ser Gly Thr Val Asn
            260                 265                 270

Tyr Leu Ala Tyr Asn Gly Asn Gly Ala
        275                 280


<210> SEQ ID NO 8
<211> LENGTH: 277
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: mature form of Genbank Accession No. ACV71845.1

<400> SEQUENCE: 8

Thr Glu Gln Ser Gly Ala Pro Trp Gly Leu Gly Arg Ile Ser His Arg
1               5                   10                  15

Gln Lys Gly Ser Thr Thr Tyr Arg Tyr Asp Asp Ser Ala Gly Glu Gly
            20                  25                  30

Thr Cys Val Tyr Ile Ile Asp Thr Gly Ile Glu Ala Ser His Pro Glu
        35                  40                  45

Phe Glu Gly Arg Ala Ala Phe Leu Lys Ser Phe Ile Ser Gly Gln Asn
    50                  55                  60

Ser Asp Gly His Gly His Gly Thr His Cys Ala Gly Thr Ile Gly Ser
65                  70                  75                  80

Arg Ala Tyr Gly Val Ala Lys Lys Ala Lys Leu Phe Gly Val Lys Val
                85                  90                  95

Leu Asp Asn Gln Gly Ser Gly Ser Tyr Ser Gly Ile Ile Ser Gly Met
            100                 105                 110

Asp Tyr Val Ala Gln Asp Ser Lys Thr Arg Gly Cys Pro Lys Gly Ala
        115                 120                 125

Ile Ala Ser Met Ser Leu Gly Gly Gly Tyr Ser Ala Ser Val Asn Gln
    130                 135                 140

Gly Ala Ala Ala Leu Val Asn Ser Gly Val Phe Leu Ala Val Ala Ala
145                 150                 155                 160

Gly Asn Asp Asn Arg Asp Ala Gln Asn Thr Ser Pro Ala Ser Glu Pro
```

-continued

```
                165                 170                 175

Ser Ala Cys Thr Val Gly Ala Thr Asp Ser Asn Asp Asn Arg Ser Ser
            180                 185                 190

Phe Ser Asn Phe Gly Arg Val Val Asp Ile Phe Ala Pro Gly Thr Gly
        195                 200                 205

Val Leu Ser Thr Trp Ile Gly Gly Ser Thr Asn Thr Ile Ser Gly Thr
    210                 215                 220

Ser Met Ala Thr Pro His Ile Ala Gly Leu Ala Ala Tyr Leu Ser Ala
225                 230                 235                 240

Ile Gln Gly Lys Thr Ser Pro Ala Ala Leu Cys Lys Leu Ile Gln Asp
                245                 250                 255

Thr Ala Thr Lys Asn Val Leu Lys Gly Val Pro Ser Gly Thr Val Asn
            260                 265                 270

Tyr Leu Ala Tyr Asn
        275


<210> SEQ ID NO 9
<211> LENGTH: 277
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: mature form of Genbank Accession No. ACV71846.1

<400> SEQUENCE: 9

Thr Asp Gln Ser Gly Ala Pro Trp Gly Leu Gly Arg Ile Ser His Arg
1               5                   10                  15

Asn Lys Gly Ser Thr Thr Tyr Arg Tyr Asp Asp Ser Ala Gly Glu Gly
            20                  25                  30

Thr Cys Val Tyr Ile Ile Asp Thr Gly Ile Glu Ala Ser His Pro Glu
        35                  40                  45

Phe Gln Gly Arg Ala Thr Phe Leu Lys Ser Phe Ile Asn Gly Gln Thr
    50                  55                  60

Ser Asp Gly His Gly His Gly Thr His Cys Ala Gly Thr Ile Gly Ser
65                  70                  75                  80

Lys Thr Tyr Gly Val Ala Lys Lys Ala Lys Leu Tyr Gly Val Lys Val
                85                  90                  95

Leu Asp Asn Gln Gly Ser Gly Ser Tyr Ser Gly Ile Ile Ser Gly Met
            100                 105                 110

Asp Tyr Val Ala Lys Asp Ser Lys Thr Arg Gly Cys Pro Lys Gly Ala
        115                 120                 125

Ile Ala Ser Met Ser Leu Gly Gly Gly Tyr Ser Ala Ser Val Asn Gln
    130                 135                 140

Gly Ala Ala Ala Leu Val Asn Ser Gly Val Phe Leu Ala Val Ala Ala
145                 150                 155                 160

Gly Asn Asp Asn Arg Asp Ala Gln Asn Thr Ser Pro Ala Ser Glu Pro
                165                 170                 175

Thr Ala Cys Thr Val Gly Ala Thr Asp Ser Gly Asp Asn Arg Ser Ser
            180                 185                 190

Phe Ser Asn Tyr Gly Arg Val Val Asp Ile Phe Ala Pro Gly Ser Asn
        195                 200                 205

Val Leu Ser Thr Trp Ile Asn Gly Gly Thr Asn Ser Ile Ser Gly Thr
    210                 215                 220

Ser Met Ala Thr Pro His Ile Ala Gly Leu Ala Ala Tyr Leu Ser Ala
```

-continued

```
225                 230                 235                 240

Leu Gln Gly Lys Thr Ser Pro Ala Ala Leu Cys Lys Lys Ile Gln Asp
                245                 250                 255

Thr Ala Thr Lys Asn Val Leu Ser Gly Val Pro Ser Gly Thr Val Asn
            260                 265                 270

Leu Leu Ala Tyr Asn
        275


<210> SEQ ID NO 10
<211> LENGTH: 275
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: mature form of Genbank Accession No. OAA81462.1

<400> SEQUENCE: 10

Thr Gln Gln Pro Gly Ala Thr Trp Gly Leu Thr Arg Ile Ser His Arg
1               5                   10                  15

Gln Arg Gly Ser Thr Ser Tyr Ala Tyr Asp Thr Ser Ala Gly Ala Gly
            20                  25                  30

Ala Cys Ala Tyr Val Ile Asp Thr Gly Val Glu Asp Thr His Pro Glu
        35                  40                  45

Phe Glu Gly Arg Ala Lys Gln Ile Lys Thr Phe Val Ser Gly Thr Arg
    50                  55                  60

Asp Gly His Gly His Gly Thr His Cys Ser Gly Thr Ile Gly Ser Lys
65                  70                  75                  80

Thr Trp Gly Val Ala Lys Lys Val Ser Ile Phe Gly Val Lys Val Leu
                85                  90                  95

Glu Asp Ser Gly Ser Gly Ser Leu Ser Gly Val Ile Ala Gly Met Asp
            100                 105                 110

Phe Val Ala Ser Asp Arg Arg Ser Arg Asn Cys Pro Lys Gly Val Val
        115                 120                 125

Ala Ser Met Ser Leu Gly Gly Gly Tyr Ser Ala Ala Val Asn Gln Ala
    130                 135                 140

Ala Ala Arg Leu Gln Ser Ser Gly Val Phe Val Ala Val Ala Ala Gly
145                 150                 155                 160

Asn Asp Asn Arg Asp Ala Ala Gln Thr Ser Pro Ala Ser Glu Pro Ser
                165                 170                 175

Val Cys Thr Val Gly Ala Thr Asp Ser Ala Asp Arg Arg Ser Thr Phe
            180                 185                 190

Ser Asn Phe Gly Arg Ala Leu Asp Ile Phe Ala Pro Gly Thr Asp Ile
        195                 200                 205

Thr Ser Thr Trp Ile Gly Gly Arg Thr Asn Thr Ile Ser Gly Thr Ser
    210                 215                 220

Met Ala Thr Pro His Ile Ala Gly Leu Gly Ala Tyr Leu Leu Ala Leu
225                 230                 235                 240

Gln Gly Gly Ser Ala Gly Thr Ile Cys Ser Arg Ile Gln Ser Leu Ser
                245                 250                 255

Thr Lys Asn Ala Ile Thr Asn Val Pro Ala Gly Thr Val Asn Tyr Leu
            260                 265                 270

Ala Phe Asn
        275
```

<210> SEQ ID NO 11
<211> LENGTH: 275
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: mature form of Genbank Accession No. OAQ97020.1

<400> SEQUENCE: 11

```
Thr Gln Gln Pro Gly Ala Thr Trp Gly Leu Thr Arg Ile Ser His Arg
1               5                   10                  15

Gln Arg Gly Ser Thr Ser Tyr Ala Tyr Asp Thr Ser Ala Gly Leu Gly
            20                  25                  30

Ala Cys Ala Tyr Val Ile Asp Thr Gly Val Glu Asp Thr His Pro Glu
        35                  40                  45

Phe Glu Gly Arg Ala Lys Gln Ile Lys Thr Phe Val Ser Gly Thr Arg
    50                  55                  60

Asp Gly His Gly His Gly Thr His Cys Ser Gly Thr Ile Gly Ser Lys
65                  70                  75                  80

Thr Trp Gly Val Ala Lys Lys Val Ser Ile Phe Gly Val Lys Val Leu
                85                  90                  95

Glu Asp Asn Gly Ser Gly Thr Leu Ser Gly Val Ile Ala Gly Met Asp
            100                 105                 110

Phe Val Ala Ser Asp Arg Arg Ser Arg Asn Cys Pro Lys Gly Val Val
        115                 120                 125

Ala Ser Met Ser Leu Gly Gly Gly Tyr Ser Ala Ala Val Asn Gln Ala
    130                 135                 140

Ala Ala Arg Leu Gln Ser Ser Gly Val Phe Val Ala Val Ala Ala Gly
145                 150                 155                 160

Asn Glu Asn Arg Asp Ala Ser Gln Thr Ser Pro Ala Ser Glu Pro Ser
                165                 170                 175

Val Cys Thr Val Gly Ala Thr Asp Ser Ala Asp Arg Arg Ser Ser Phe
            180                 185                 190

Ser Asn Phe Gly Arg Ala Leu Asp Ile Phe Ala Pro Gly Thr Asp Ile
        195                 200                 205

Thr Ser Thr Trp Ile Gly Gly Arg Thr Asn Thr Ile Ser Gly Thr Ser
    210                 215                 220

Met Ala Thr Pro His Ile Ala Gly Leu Gly Ala Tyr Leu Leu Ala Leu
225                 230                 235                 240

Gln Gly Gly Asn Ala Glu Thr Ile Cys Ser Arg Ile Gln Ser Leu Ser
                245                 250                 255

Thr Lys Asn Val Ile Ser Gly Val Pro Ala Gly Thr Val Asn Tyr Leu
            260                 265                 270

Ala Phe Asn
        275
```

<210> SEQ ID NO 12
<211> LENGTH: 8
<212> TYPE: PRT
<213> ORGANISM: Artificial Sequence
<220> FEATURE:
<223> OTHER INFORMATION: Synthetic construct

<400> SEQUENCE: 12

```
Val Ala Gly Leu Ala Ala Tyr Leu
1               5
```

<210> SEQ ID NO 13
<211> LENGTH: 8
<212> TYPE: PRT
<213> ORGANISM: Artificial Sequence
<220> FEATURE:
<223> OTHER INFORMATION: Synthetic construct

<400> SEQUENCE: 13

Val Ala Gly Leu Ala Ala His Leu
1 5

<210> SEQ ID NO 14
<211> LENGTH: 8
<212> TYPE: PRT
<213> ORGANISM: Artificial Sequence
<220> FEATURE:
<223> OTHER INFORMATION: Synthetic construct

<400> SEQUENCE: 14

Val Ala Gly Leu Ala Ala Gln Leu
1 5

<210> SEQ ID NO 15
<211> LENGTH: 8
<212> TYPE: PRT
<213> ORGANISM: Artificial Sequence
<220> FEATURE:
<223> OTHER INFORMATION: Synthetic construct

<400> SEQUENCE: 15

Val Ala Gly Leu Ala Ala Lys Leu
1 5

<210> SEQ ID NO 16
<211> LENGTH: 8
<212> TYPE: PRT
<213> ORGANISM: Artificial Sequence
<220> FEATURE:
<223> OTHER INFORMATION: Synthetic construct

<400> SEQUENCE: 16

Val Ala Gly Leu Ala Ala Glu Leu
1 5

<210> SEQ ID NO 17
<211> LENGTH: 8
<212> TYPE: PRT
<213> ORGANISM: Artificial Sequence
<220> FEATURE:
<223> OTHER INFORMATION: Synthetic construct

<400> SEQUENCE: 17

Val Ala Gly Leu Ala Ala Arg Leu
1 5

<210> SEQ ID NO 18
<211> LENGTH: 8
<212> TYPE: PRT
<213> ORGANISM: Artificial Sequence
<220> FEATURE:
<223> OTHER INFORMATION: Synthetic construct

<400> SEQUENCE: 18

Val Ala Gly Leu Ala Ala Gly Leu
1 5

<210> SEQ ID NO 19
<211> LENGTH: 8
<212> TYPE: PRT
<213> ORGANISM: Artificial Sequence
<220> FEATURE:
<223> OTHER INFORMATION: Synthetic construct

<400> SEQUENCE: 19

Val Ala Gly Leu Ala Ala Phe Leu
1 5

<210> SEQ ID NO 20
<211> LENGTH: 8
<212> TYPE: PRT
<213> ORGANISM: Artificial Sequence
<220> FEATURE:
<223> OTHER INFORMATION: Synthetic construct

<400> SEQUENCE: 20

Val Ala Gly Leu Ala Ala Val Leu
1 5

<210> SEQ ID NO 21
<211> LENGTH: 8
<212> TYPE: PRT
<213> ORGANISM: Artificial Sequence
<220> FEATURE:
<223> OTHER INFORMATION: Synthetic construct

<400> SEQUENCE: 21

Val Ala Gly Leu Ala Ala Asp Leu
1 5

<210> SEQ ID NO 22
<211> LENGTH: 8
<212> TYPE: PRT
<213> ORGANISM: Artificial Sequence
<220> FEATURE:
<223> OTHER INFORMATION: Synthetic construct

<400> SEQUENCE: 22

Val Ala Gly Leu Ala Ala Thr Leu
1 5

<210> SEQ ID NO 23
<211> LENGTH: 8
<212> TYPE: PRT
<213> ORGANISM: Artificial Sequence
<220> FEATURE:
<223> OTHER INFORMATION: Synthetic construct

<400> SEQUENCE: 23

Val Ala Gly Leu Ala Ala Leu Leu
1 5

<210> SEQ ID NO 24
<211> LENGTH: 8
<212> TYPE: PRT
<213> ORGANISM: Artificial Sequence
<220> FEATURE:
<223> OTHER INFORMATION: Synthetic construct

<400> SEQUENCE: 24

Val Ala Gly Leu Ala Ala Ile Leu
1 5

<210> SEQ ID NO 25

-continued

```
<211> LENGTH: 8
<212> TYPE: PRT
<213> ORGANISM: Artificial Sequence
<220> FEATURE:
<223> OTHER INFORMATION: Synthetic construct

<400> SEQUENCE: 25

Val Ala Gly Leu Ala Ala Met Leu
1               5


<210> SEQ ID NO 26
<211> LENGTH: 8
<212> TYPE: PRT
<213> ORGANISM: Artificial Sequence
<220> FEATURE:
<223> OTHER INFORMATION: Synthetic construct

<400> SEQUENCE: 26

Val Ala Gly Leu Ala Ala Ser Leu
1               5


<210> SEQ ID NO 27
<211> LENGTH: 8
<212> TYPE: PRT
<213> ORGANISM: Artificial Sequence
<220> FEATURE:
<223> OTHER INFORMATION: Synthetic construct

<400> SEQUENCE: 27

Val Ala Gly Leu Ala Ala Trp Leu
1               5


<210> SEQ ID NO 28
<211> LENGTH: 8
<212> TYPE: PRT
<213> ORGANISM: Artificial Sequence
<220> FEATURE:
<223> OTHER INFORMATION: Synthetic construct

<400> SEQUENCE: 28

Val Ala Gly Leu Ala Ala Pro Leu
1               5


<210> SEQ ID NO 29
<211> LENGTH: 8
<212> TYPE: PRT
<213> ORGANISM: Artificial Sequence
<220> FEATURE:
<223> OTHER INFORMATION: Synthetic construct

<400> SEQUENCE: 29

Val Ala Gly Leu Ala Ala Asn Leu
1               5


<210> SEQ ID NO 30
<211> LENGTH: 8
<212> TYPE: PRT
<213> ORGANISM: Artificial Sequence
<220> FEATURE:
<223> OTHER INFORMATION: Synthetic construct

<400> SEQUENCE: 30

Val Ala Gly Leu Ala Ala Asn Leu
1               5


<210> SEQ ID NO 31
<211> LENGTH: 8
```

-continued

```
<212> TYPE: PRT
<213> ORGANISM: Artificial Sequence
<220> FEATURE:
<223> OTHER INFORMATION: Synthetic construct

<400> SEQUENCE: 31

Val Ala Gly Leu Ala Ala Cys Leu
1               5


<210> SEQ ID NO 32
<211> LENGTH: 4
<212> TYPE: PRT
<213> ORGANISM: Artificial Sequence
<220> FEATURE:
<223> OTHER INFORMATION: Synthetic construct

<400> SEQUENCE: 32

Ala Ala Pro Phe
1
```